US010751154B2

(12) United States Patent
Rahmel et al.

(10) Patent No.: US 10,751,154 B2
(45) Date of Patent: Aug. 25, 2020

(54) INHALER

(71) Applicant: Boehringer Ingelheim Vetmedica GmbH, Ingelheim am Rhein (DE)

(72) Inventors: Marcus Rainer Rahmel, Ockenheim (DE); Andree Jung, Idar-Oberstein (DE); Herbert Wachtel, Ingelheim am Rhein (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 587 days.

(21) Appl. No.: 15/301,215

(22) PCT Filed: Mar. 27, 2015

(86) PCT No.: PCT/EP2015/000656
§ 371 (c)(1),
(2) Date: Sep. 30, 2016

(87) PCT Pub. No.: WO2015/149921
PCT Pub. Date: Oct. 8, 2015

(65) Prior Publication Data
US 2017/0014215 A1 Jan. 19, 2017

(30) Foreign Application Priority Data

Mar. 31, 2014 (EP) ..................................... 14001180

(51) Int. Cl.
*A61M 15/00* (2006.01)
*A61D 7/04* (2006.01)

(52) U.S. Cl.
CPC ............. *A61D 7/04* (2013.01); *A61M 15/009* (2013.01); *A61M 15/0073* (2014.02); *A61M 15/0086* (2013.01); *A61M 2250/00* (2013.01)

(58) Field of Classification Search
CPC ...... A61G 3/02; A61G 3/0245; A61G 3/0263; A61G 3/0272; A61G 3/029; A61G 3/061; A61G 3/0833; A61M 11/003; A61M 15/00; A61M 15/0065; A61M 15/0068; A61M 15/0075; A61M 15/0081; A61M 15/0086; A61M 15/009; A61M 15/08; A61M 2202/064; B05B 11/0038; B05B 11/3009; B05B 11/3019; B05B 11/3052; B05B 11/3056; B05B 11/3057; B05B 11/3059;
(Continued)

(56) References Cited

U.S. PATENT DOCUMENTS 4,706,663 A * 11/1987 Makiej ................. A61M 15/00
128/200.18
5,368,231 A 11/1994 Brunerie et al.
(Continued)

FOREIGN PATENT DOCUMENTS

FR  2 812 826 B1  2/2002

*Primary Examiner* — Annette Dixon
(74) *Attorney, Agent, or Firm* — David S. Safran; Roberts Calderon Safran & Cole, P.C.

(57) ABSTRACT

An insert which can be inserted into an inhaler, particularly for a horse has a reservoir for a medicament preparation held under excess pressure and a valve. The insert also has a nebulizer that is held directly on the reservoir and a discharge nozzle, associated with the nebulizer and fluidically connected to the valve, for forming an aerosol with the medicament preparation.

26 Claims, 12 Drawing Sheets

Figure 1:
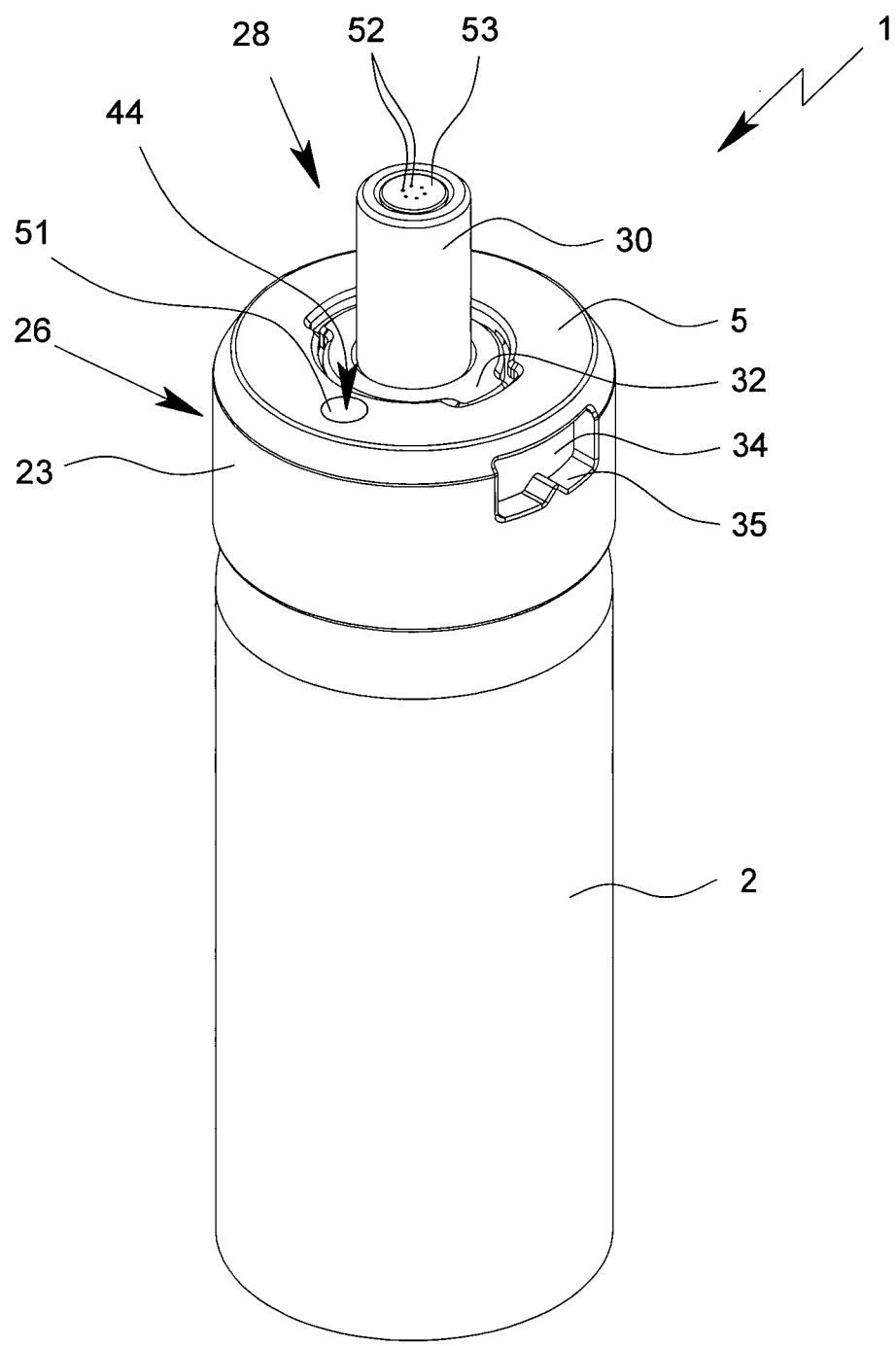
Figure 2:
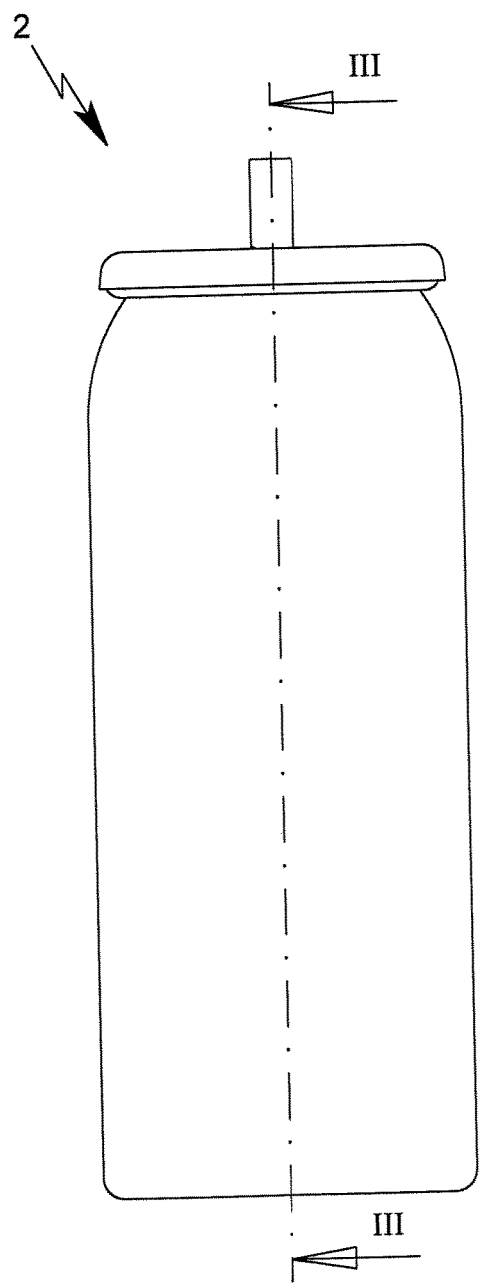

(58) Field of Classification Search
CPC ............. B05B 11/3076; B05B 11/3077; B05B 11/3092; B60P 1/43; B65D 83/226; B65D 83/386; B65G 19/02; G06M 1/045; G06M 1/248
See application file for complete search history.

(56) References Cited

U.S. PATENT DOCUMENTS

| | | | |
|---|---|---|---|
| 5,392,768 A * | 2/1995 | Johansson | A61M 15/00 128/200.14 |
| 5,666,948 A | 9/1997 | Matson | |
| 5,950,619 A * | 9/1999 | van der Linden | A61M 15/0065 128/200.14 |
| 6,189,739 B1 | 2/2001 | von Schuckmann | |
| 6,588,631 B2 | 7/2003 | Sanchez | |
| 6,769,601 B2 * | 8/2004 | Haikarainen | A61M 15/0065 235/87 R |
| 6,951,215 B1 | 10/2005 | Hoffman | |
| 6,959,708 B1 | 11/2005 | Rasor et al. | |
| 7,267,120 B2 | 9/2007 | Rustad et al. | |
| 7,717,299 B2 * | 5/2010 | Greiner-Perth | B05B 11/3052 222/162 |
| 8,235,044 B2 | 8/2012 | Fletcher | |
| 9,156,048 B2 * | 10/2015 | Le Maner | A61M 15/009 |
| 2012/0103326 A1 * | 5/2012 | Karle | A61D 7/04 128/200.21 |
| 2012/0138049 A1 | 6/2012 | Wachtel | |
| 2013/0312740 A1 | 11/2013 | Pardonge | |
| 2014/0083424 A1 | 3/2014 | Hoekman et al. | |

\* cited by examiner

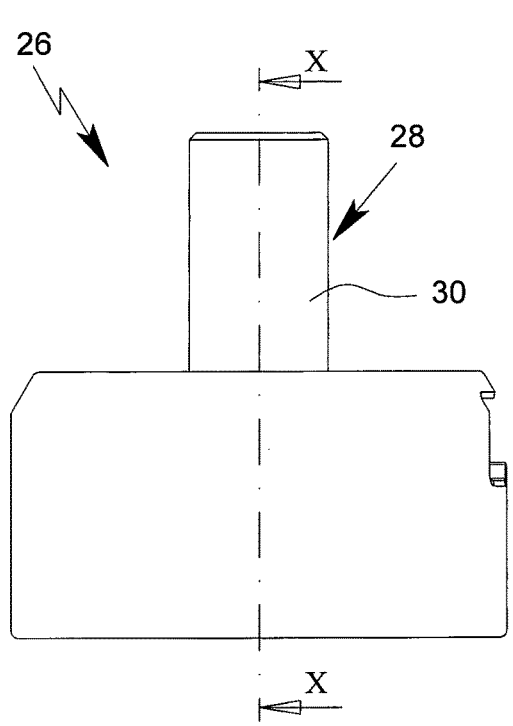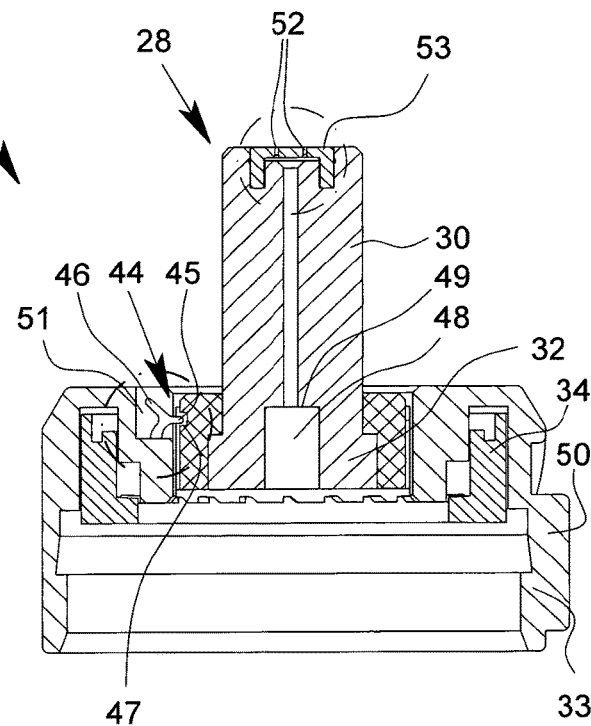
Fig. 9    Fig. 10
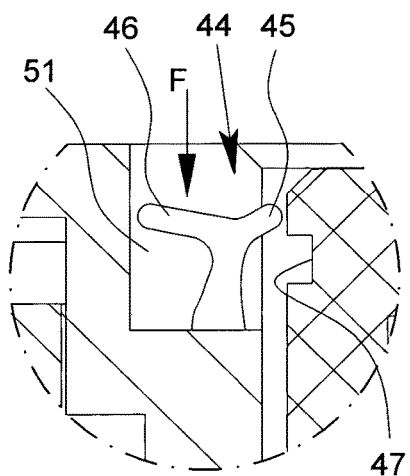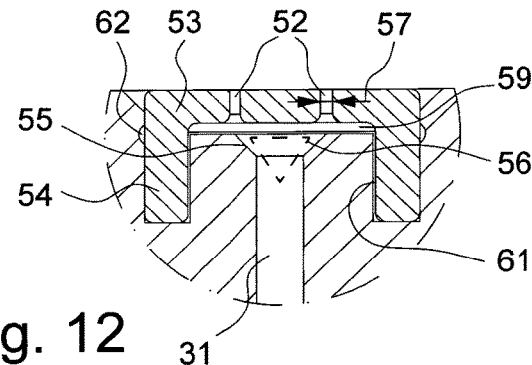
Fig. 11    Fig. 12
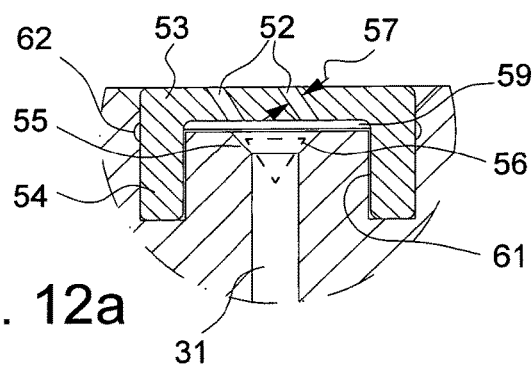
Fig. 12a

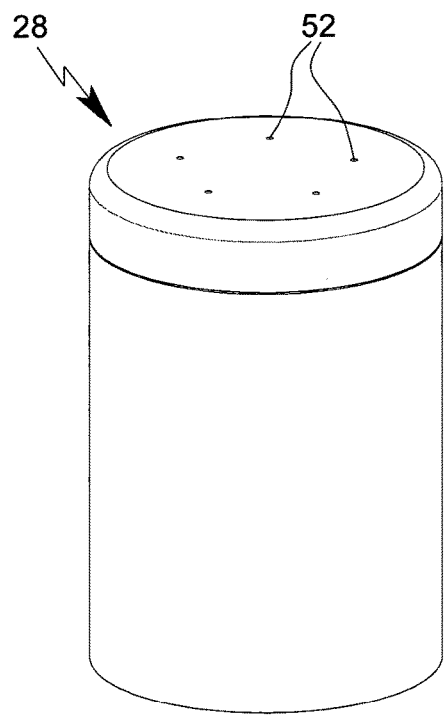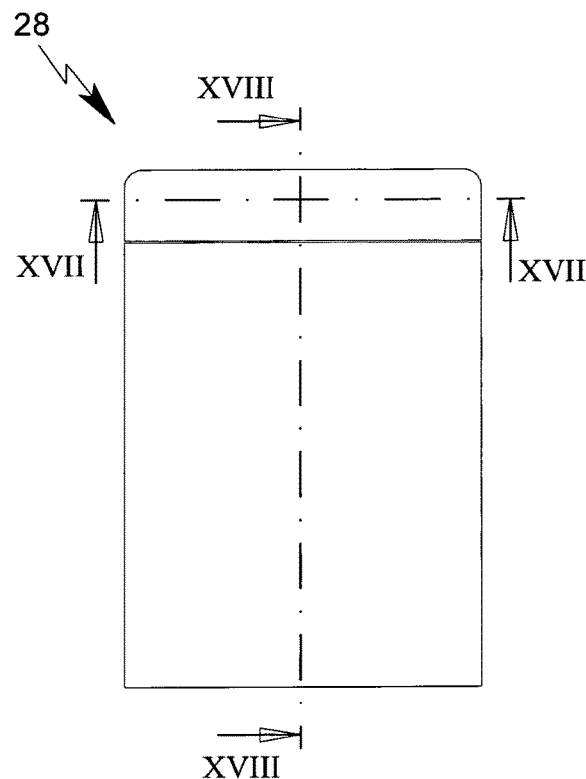
Fig. 15
Fig. 16
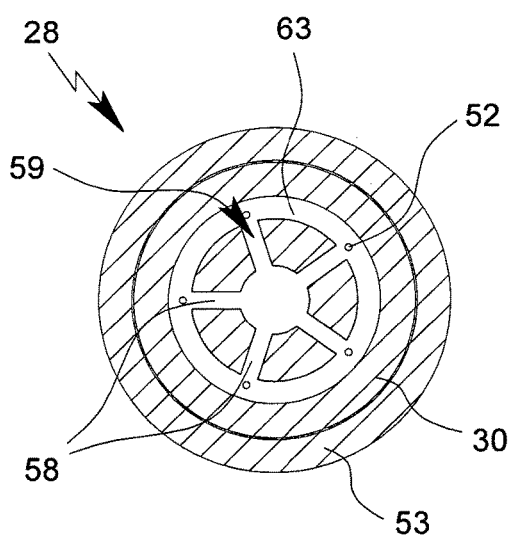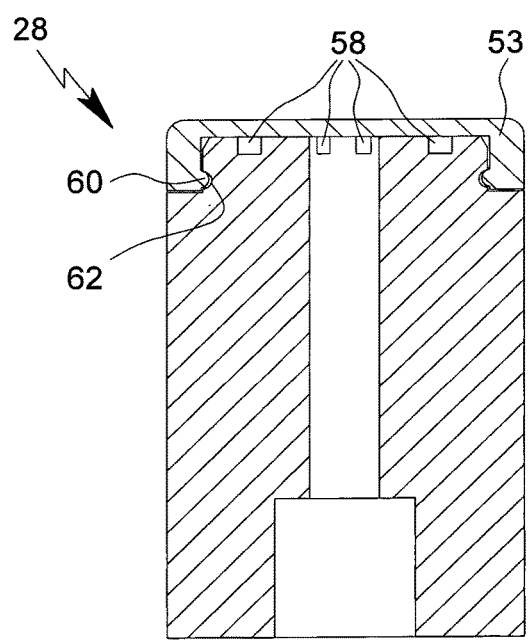
Fig. 17
Fig. 18

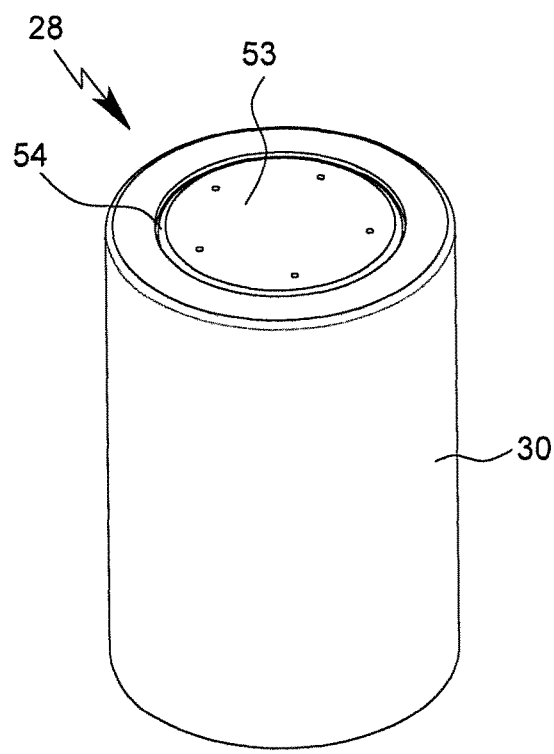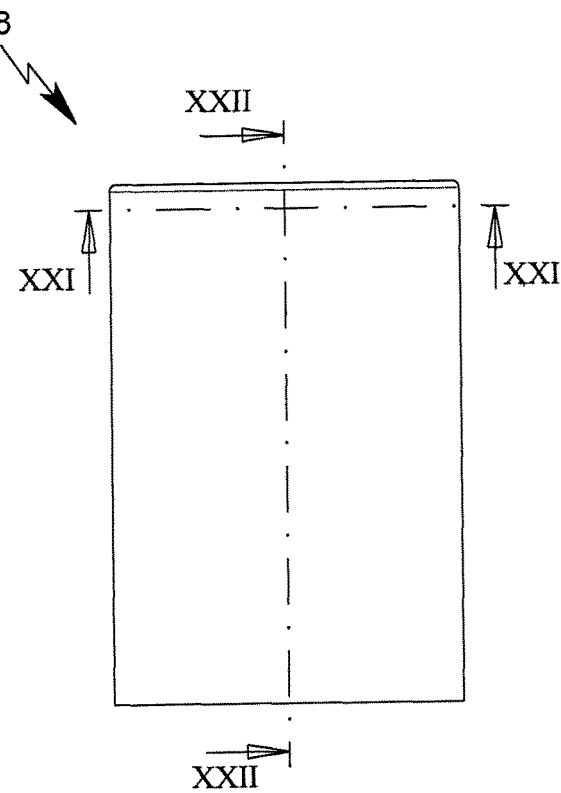
Fig. 19  Fig. 20
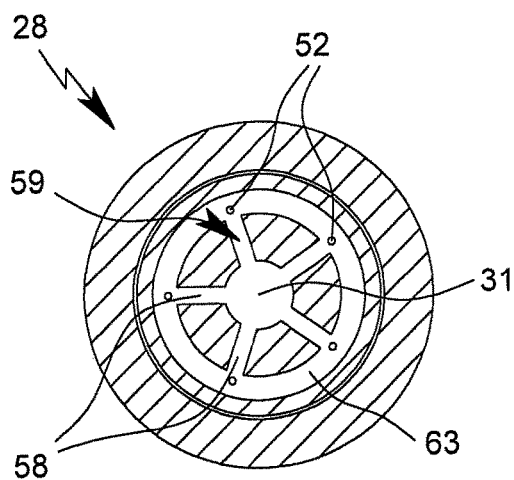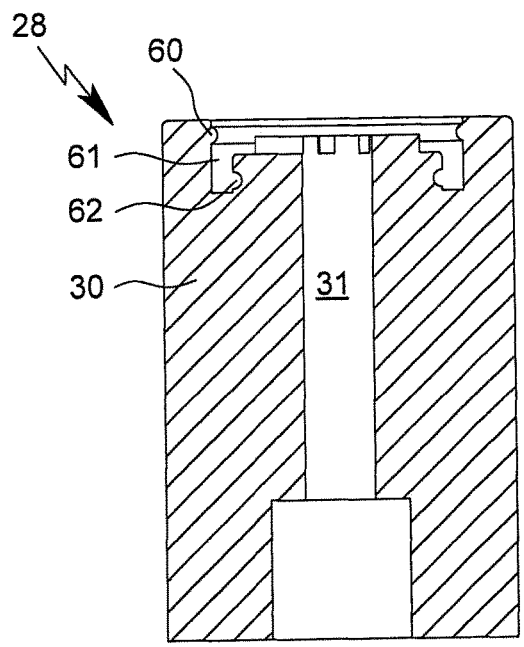
Fig. 21  Fig. 22

INHALER

BACKGROUND OF THE INVENTION

Field of the Invention

The present invention relates to an insert for an inhaler as well as an inhaler. In particular, the present invention relates to inhalers for horses or other large animals, with an adapter for a nostril or other respiratory orifice.

Description of Related Art

The invention further relates to inhalers which, on each actuation, dispense a defined dose or amount of a medicinal fluid held under excess pressure, for which reason these inhalers are also known as "pressurized metered-dose inhalers" (pMDI).

A pMDI has a reservoir, which is filled with a medicament preparation and is kept under pressure by means of a propellant gas. The reservoir further comprises a metering valve for dispensing the medicament fluid. The metering valve is able to dispense a specified or measured amount of the medicament fluid each time the valve is activated. The fluid is dispensed by the movement of a valve element of the metering valve.

U.S. Pat. No. 5,666,948 A discloses a pMDI with a nostril adapter for a horse. During operation, the reservoir is normally used above the animal's head or with the valve directed downwards. A valve element of the valve is connected to the inhaler and the reservoir is movable relative to the inhaler or the valve element. For activation, the reservoir can be pressed downwards manually or be pulled down by means of a trigger button, thus dispensing a dose of the medicament fluid.

In conjunction with their use in large animals, such as horses, inhalers have the disadvantage of requiring a very robust, relatively large and complex construction, which is expensive to manufacture. At the same time, their use in large animals, unless the animals are physically restrained, rapidly leads to soiling by secretions or the like, which prevent longer-term use or re-use of the inhaler.

SUMMARY OF THE INVENTION

The object of the present invention is therefore to provide an insert and an inhaler, which will give long and reliable service with economical use of materials, particularly when used on large animals such as horses.

The above object is achieved by an insert and an inhaler as described herein.

In a first aspect, the present invention relates to an insert, which can be inserted in an inhaler, particularly for a horse. This insert comprises a reservoir with a valve for a medicament preparation held under excess pressure. In addition, the insert comprises a nebulizer held directly on the reservoir and a discharge nozzle associated with the nebulizer and fluidically connected to the valve, for forming an aerosol with the medicament preparation.

The terms "discharge" and "dispensing" are preferably synonymous or interchangeable. In the following description, purely for greater clarity, the term "discharge" is always used, without loss of generality, in conjunction with the discharge nozzle or the aerosol formation and the term "dispensing" is used in conjunction with the aerosol that has already been produced.

A discharge nozzle in the sense of the present invention is preferably a nozzle, which is suitable for dispensing the medicament preparation while preferably forming an aerosol that is able to be respirated. In particular, the discharge nozzle is a nozzle, which is suitable for nebulizing liquids.

A direction of discharge according to the present invention preferably is a main or primary direction of discharge, in particular of the discharge nozzle or nozzle opening(s) of the discharge nozzle. In particular, the direction of discharge corresponds to or at least essentially complies with a middle axis or center axis of a spray mist or spray cone produced while forming the aerosol. The direction of discharge according to the present invention preferably at least essentially corresponds to or complies with a (symmetry or middle) axis of nozzle openings of the discharge nozzle.

The proposed insert can preferably be inserted into an inhaler and/or removed from an inhaler. In particular, the insert can be accommodated or received by the inhaler for use. The insert may be exchangeable, as a result of which an inhaler is suitable for repeated or universal use.

The nebulizer is preferably non-detachably connected or connectable to the reservoir. In particular, the nebulizer is clipped onto the reservoir or otherwise held thereon, preferably by latching. In this way a construction unit can be formed with the nebulizer and the reservoir, thus doing away with the replacement of individual parts.

The discharge nozzle is particularly preferably held and/or mounted on the reservoir by means of the nebulizer. In this way, a construction unit can be formed with the nebulizer, the reservoir and the discharge nozzle.

Preferably, the discharge nozzle is secured against removal, taking off or pulling off, by means of the nebulizer, or in the nebulizer. The discharge nozzle is thus preferably inseparable from the insert, from the nebulizer or from the reservoir. In this way, it can be ensured that replacement of the reservoir is accompanied by the replacement of the discharge nozzle.

Preferably, the nebulizer is inseparably held on the reservoir. In particular, the nebulizer and/or the discharge nozzle form an inseparable construction unit with the reservoir, and preferably, with the valve. The inseparable construction unit ensures that the discharge nozzle is changed when the reservoir is exchanged or when the inhaler is reused.

"Inseparable" or "undetachable" or "permanent" in the sense of the present invention means, in particular that, at least after assembly is complete, separation is only possible with great effort, cannot be done without tools or manually and is possible only by damaging or destroying the item.

Particularly when used in connection with animals, the discharge nozzle may have a tendency to become clogged or otherwise blocked up with secretions or the like. The proposed insert, by providing for only total replacement or by the formation of the inseparable construction unit, advantageously makes it possible to prevent possibly unreliable, blocked or worn discharge nozzles from being re-used with a new or freshly filled reservoir. Consequently, when the inhaler is reused, reliable operation and dosing can be guaranteed.

The proposed insert ensures that the valve, particularly a metering chamber volume of the valve, corresponds to or is adapted to a concentration of active substance in the medicament preparation. In this way, correct dosing can be ensured.

The metering chamber volume is preferably more than 200 µl, particularly preferably more than 250 µl, particularly more than 300 µl and/or less than 1000 µl, preferably less than 800 µl, particularly less than 600 or 400 µl. A metering chamber volume of 280 µl to 340 µl is most particularly preferred. It is possible to use the inhaler universally for different large animals and at the same time minimize of number of necessary actuation steps. In particular, only one to three actuations or a total dose of between 300 µl and 900 µl are particularly advantageous.

With the proposed insert, it can be ensured, alternatively or additionally, that the valve, particularly a metering chamber volume of the valve, corresponds to or fits the discharge nozzle.

Preferably, a dose of the medicament preparation or a metering chamber volume of the valve can be converted into an, in particular, respirable aerosol within a sufficiently short time span, preferably within a time span of less than a second, particularly less than half a second. Therefore, it is preferable for the discharge nozzle to be able to dispense at least one metering chamber volume per second, preferably at least twice the metering chamber volume per second.

Too small a metering chamber volume in relation to the amount discharged may lead to inaccuracies of dosing. Therefore, it is preferable if the discharge nozzle is able to dispense less than ten times the metering chamber volume per second.

With the proposed insert, an optimum ratio of metering chamber volume of the valve to the discharge speed of the discharge nozzle is obtained, leading to good reliability and metering accuracy.

With the proposed insert it may alternatively or additionally be ensured that a discharge nozzle suited to the particularly medicament preparation is used. In particular, the discharge nozzle may suit the properties of the medicament preparation, particularly its viscosity and flow properties. In this way, accurate dosing and/or a sufficiently fine aerosol can be obtained.

Overall, with the proposed insert, it can be ensured that a combination of medicament preparation, valve and discharge nozzle is always used which leads to reliable dosing and aerosol formation. The proposed insert thus ensures satisfactory cooperation of the components even when an inhaler is re-used.

The discharge nozzle can be guided by the nebulizer in axial, linear and/or rotationally connected manner. As a result of the axial or linear guiding, the valve can be reliably actuated by the discharge nozzle or by movement of the discharge nozzle. As a result of rotationally connected guiding, it can be ensured that the orientation of the discharge nozzle remains unchanged.

The discharge nozzle may be axially movable for opening the valve or dispensing the medicament preparation. However, it is preferable if this axial mobility of the discharge nozzle is restricted at least to the direction of removal or dispensing for the medicament preparation or to a direction leading away from the reservoir, particularly by the nebulizer.

The discharge nozzle is preferably fluidically connected to the valve. It is also preferable if the discharge nozzle is mechanically connected to the valve, particularly to a valve element of the valve. In this way, axial movement of the discharge nozzle can move the valve element. The medicament preparation can be dispensed by the movement of the valve element. Thus, a preferably axial movement of the discharge nozzle can open the valve and activate the dispensing of the medicament preparation.

"Axial" in the sense of the present invention is preferably a movement or direction along or parallel to the central axis or an axis of symmetry of the reservoir or the insert or a movement or direction along or parallel to an axis of symmetry of the valve or valve element. In particular, the central axis corresponds to the axis of symmetry or vice versa. Moreover, the terms "central axis" or "axis of symmetry" preferably relate to a position of use of the insert or the valve. In particular, reference to the central axis or axis of symmetry is also possible irrespective of whether the insert has been inserted into the inhaler or the like.

Preferably, the direction of actuation is axial and/or corresponds or complies with a direction of movement or direction along or parallel to the central axis or an axis of symmetry of the reservoir or the insert or a movement or direction along or parallel to an axis of symmetry of the valve or valve element.

For dispensing the medicament preparation, it is preferable for the valve to be opened. In this way, medicament preparation is able to reach intake openings of the discharge nozzle and be dispensed through the dispensing openings. Preferably, the medicament preparation is dispensed through the discharge openings under a corresponding pressure or at a corresponding velocity or the like such that the aerosol is formed.

In a variant, different proposed inserts with, in particular, different medicament preparations can be used one after the other or alternately in the same inhaler. By using inserts with different medicament preparations, a respirable aerosol based on different medicament preparations can be produced and dispensed with the same inhaler or type of inhaler. This allows the inhaler to be used universally and produced efficiently in large production runs.

Features of the medicament preparation are preferably visible or displayed on the inhaler, for example, through a window in the inhaler. This can prevent mix-ups.

Alternatively or additionally, an insert may, in particular, be mechanically insertable into, or usable in, only one corresponding inhaler. The insert is preferably coded in the manner described, or in some other way, for a corresponding inhaler, particularly by orientation means, which will be discussed in more detail hereinafter. This, too, can prevent mix-ups.

The insert is preferably not designed for self-sufficient operation or cannot be used on its own as an inhaler. Preferably, the insert is protected from actuation separate from an inhaler, or is otherwise embodied for use solely with or in an inhaler.

The insert is preferably free from adapters for respiratory orifices.

The insert is preferably configured to avoid, prevent or block the dispensing of medicament without the inhaler.

The insert may comprise a cover, particularly a cap, which covers the discharge nozzle or prevents the medicament preparation from being dispensed from the inhaler.

Particularly preferably, the insert comprises a blocking device, which is embodied to prevent accidental actuation, actuation in the non-inserted state of the insert and/or actuation after reaching or exceeding a given number of actuating steps. This can prevent accidental actuation independently of the inhaler, which could have an effect on other living creatures particularly in the case of medicaments for large animals.

Alternatively or additionally, actuation can be prevented once a given number of actuation processes has been reached or exceeded. This can be done by means of the blocking device and/or the counter. The advantage of this is that actuation is prevented when the dosage might possibly be inaccurate, particularly when there is a reduction in the pressure in the reservoir or the like.

In another aspect of the present invention, the insert or the nebulizer may be configured to dispense the medicament preparation in a direction of discharge which corresponds at least substantially to a central axis of the reservoir and/or which extends diagonally with respect to the central axis of the reservoir. This has the advantage that no or very little deflection of the medicament preparation is needed and consequently a loss in pressure can be minimized.

It is particularly preferred if the direction of discharge is inclined by more than 5°, particularly more than 10° or 15° and/or less than 50°, preferably less than 45° or 40°, particularly less than 35° relative to the central axis of the reservoir or if such an angle is enclosed between the central axis and the direction of discharge. This advantageously makes it possible to prevent aerosol being deposited on the walls of a chamber for holding and temporarily storing aerosol or on the walls of an adapter for a respiratory orifice, particularly while the aerosol can be dispensed from the chamber or through the adapter for the respiratory orifice, laterally and/or in a skewed manner with respect to the central axis of the reservoir. The dispensing of the aerosol in laterally offset or skewed manner with respect to the central axis of the reservoir has advantages in terms of the anatomical shaping and consequent ease of handling of the inhaler.

In another aspect, the discharge nozzle may comprise at least three, preferably at least four discharge openings. The discharge openings may have a cumulative outlet surface area of more than $0.1$ mm$^2$, preferably more than $0.15$ mm$^2$. This has proved favorable for rapid dispensing or formation of the preferably respirable aerosol.

The insert or the nebulizer may comprise a counter, which can be driven by the triggering of the dispensing of the medicament preparation. The counter preferably forms an inseparable construction unit with the reservoir and/or with the nebulizer and/or the dispensing nozzle and/or the valve. This ensures that an insert that has already been emptied or partially emptied can be recognized as such independently of an inhaler. The counter is preferably rotatable mounted in the nebulizer.

The insert or the nebulizer preferably comprises, in particular, an axially movable activating element, the medicament preparation being adapted to be dispensed by the movement of the activating element.

The activating element is preferably embodied to move the valve element or to open the valve by some other means.

The counter may be drivable by the movement of the activating element.

The activating element may be blocked and released by the total insertion of the insert in the intended orientation.

Preferably, the activating element guides and/or moves the discharge nozzle in the nebulizer.

The activating element may be arranged between the discharge nozzle and a housing of the nebulizer held on the reservoir.

The activating element is preferably fixed to the discharge nozzle or formed by the discharge nozzle. The activating element may be held by latching on the housing. This allows a quick and easy and/or non-separable assembly. In particular, the activating element is or forms a shoulder for the axial movement of the discharge nozzle.

In one variant, the activating element is movable independently of the discharge nozzle. In this case, the discharge nozzle can be immovably held by the nebulizer and/or on the reservoir.

The insert or the nebulizer may comprise a frame or a shoulder, which is immovable with respect to the reservoir, the activating element being adjacent to the frame or the shoulder. The frame or the shoulder may surround, enclose and/or envelop the activating element. In this way, accidental triggering can be prevented.

The frame or the shoulder may be connected to the nebulizer or be formed by the nebulizer, particularly by a housing of the nebulizer, which is connected or connectable to the reservoir. However, other solutions are also possible.

Another aspect of the present invention which can also be implemented independently relates to an inhaler with a holder for a proposed insert, or an inhaler into which a proposed insert has been inserted.

Particularly preferably, in the inhaler, the reservoir and the discharge nozzle are replaceable jointly, as a combination or as a construction unit. This ensures that the correct discharge nozzle is used for the particularly medicinal fluid. Moreover, the risk of malfunction is reduced, as the discharge nozzle which may have a tendency to become blocked when coming into contact with secretions or the like is automatically replaced as well during a refilling operation.

The inhaler may comprise a chamber for holding and temporarily storing aerosol. This assists with synchronization of the administration of aerosol, particularly in large animals.

In another aspect of the present invention, the reservoir is or may be secured in position in the inhaler, at least in the axial direction. The reservoir is held by interlocking engagement, in particular, in the inhaler. This is to prevent axial movement at least when the inhaler is in operation.

Usually, the reservoir is moved to activate inhalers. Surprisingly, it has been found that fixing the reservoir with respect to the inhaler housing, the chamber and/or the adapter for the respiratory orifice, enables actuation to be carried out more easily, cheaply and precisely, when using an operating element such as an operating lever. This gives rise to advantages in terms of the handling properties of the inhaler as a whole, particularly for use on large animals such as horses.

In another aspect of the present invention, the discharge nozzle in the inhaler may also have, independently of the insert, a direction of discharge which is inclined by more than 5°, preferably more than 10° or 15° and/or less than 50°, preferably less than 45° or 40°, particularly 35°, relative to a central axis of the reservoir or a direction of actuation for dispensing the aerosol.

Preferably, the inhaler comprises an adapter for a respiratory orifice, with a dispensing opening in a direction of dispensing, or with a channel which runs in the direction of dispensing and leads in the direction of the dispensing opening. The direction of dispensing is laterally offset and/or skewed relative to a central axis of the reservoir or the discharge nozzle. This has advantages with respect to anatomical shape and consequent ease of handling of the inhaler.

Thanks to the substantially straight or only slightly inclined direction of dispensing, depositing of aerosol on walls can be avoided while at the same time allowing good handling of the inhaler. The inclination of the direction of dispensing of the discharge nozzle thus makes it possible to design an inhaler with good metering accuracy which is easy to handle and ergonomic, even when used on large animals.

According to another aspect of the present invention, the reservoir comprises a dispensing valve arranged on the top in the position of use of the inhaler. The use of a reservoir in an upright position or with the dispensing valve at the top is unusual in inhalers. However, it has been found that such a configuration, particularly in inhalers for large animals, allows a substantially more compact, inexpensive and ergonomic construction which is economical with materials, compared with the overhead operation with a valve at the bottom which is conventional in inhalers.

Preferably, the reservoir comprises a riser tube which is fluidically connected to the valve. This provides a simple and inexpensive way of dispensing the medicament preparation with the valve at the top. Alternatively or additionally, the medicament preparation may be held in a pouch which is arranged in the reservoir and is externally pressurized.

Moreover, the inhaler preferably comprises a lever-like actuating element, this has proved advantageous for opening the valve that is directed upwardly, even under rough conditions.

The inhaler preferably has a holder for the proposed insert, wherein the insert comprising the reservoir is axially insertable into the holder and/or has been inserted into the inhaler. As a result, the inhaler can be re-used.

The holder may comprise a retaining portion for at least axially retaining the reservoir or the insert comprising the reservoir. In particular, the retaining portion may be, or comprise, a flap or latching means. In this way, it is possible to secure the reservoir in the inhaler, in particular, even if the insert is exchangeable.

The holder is preferably formed by or in a handle or gripping means. This allows a large gripping surface. This is advantageous for use with large animals such as horses, particular when the user is wearing gloves, while at the same time producing a compact inhaler.

It is preferable if the holder is formed in the gripping surface and/or the gripping surface is formed around the holder. This synergistically results in a saving of space and on materials.

The holder preferably comprises an orientation portion for orienting the insertion of the insert. In this way, the dispensing direction for the aerosol can be fixed, particularly when the chamber is inclined relative to the central axis of the reservoir, the insert and/or the discharge nozzle.

The holder may alternatively or additionally comprise a release portion for releasing the dispensing of the medicament preparation by insertion of the insert. This ensures that the medicament preparation can only be dispensed when the insert has been inserted fully and/or correctly. This is for safety reasons, as, particularly in the case of medicaments for large animals, accidental release from the inhaler could have unforeseen effects.

Preferably, the orientation portion comprises the release portion or vice versa, and preferably the dispensing of the medicament preparation can be released by fully inserting the insert in the intended orientation. The orientation portion and the release portion may synergistically be the same part, thus saving on construction and materials.

The holder for the inhaler or the insert may be coded, so that the inhaler and the insert correspond to one another and in particular can only be used in combination. Such coding may be provided by the orientation portion, the release portion or the orientation element or release element. However, other solutions are also possible. In particular, coding may be provided by mechanical compatibility of the insert with the holder, without this necessarily having to be accompanied by a particular orientation. A combination is particularly preferred, however, as it provides a simple, robust and inexpensive solution.

According to another aspect of the present invention, the inhaler may comprise an exchangeable counter, the counter preferably being insertable into the holder. In particular, the counter may be exchanged together with the insert. However, the counter may also be capable of being inserted into the inhaler or exchanged separately. The possibility of exchanging it means that if the inhaler is used several times the correct count for the particular reservoir can always be displayed.

It is possible that the inhaler has some or all of the components of the insert or that some or all of the components of the insert are individually replaceable. However, the inhaler is particularly preferably of modular construction. Therefore, the invention is described with reference to an insert for the inhaler or in the inhaler. It should be understood that the inhaler may also comprise the parts of the insert without being an insert. In particular, the insert may be fixedly installed so that it cannot be replaced or removed being integrated in the inhaler in a permanent manner, even though it is preferable for the insert to be insertable, removable or replaceable.

A further aspect of the present invention, which can also be implemented independently, relates to a medical use of the insert, the reservoir, the nebulizer and/or the inhaler, in particular as described above.

In a further aspect the present invention concerns the insert, the reservoir, the nebulizer and/or the inhaler for the use (in a method) for the management/treatment, preferably of airway disease, in particular in equines, preferably horses, preferably wherein the airway disease is a pulmonary disease, more preferably the airway disease is selected from the group consisting of: recurrent airway obstruction (RAO), summer pasture associated obstructive pulmonary disease (SPAOPD), and inflammatory airway disease (IAD).

The invention further concerns a method of treating an airway disease comprising administering a therapeutic effective amount of an active substance or a pharmaceutically acceptable salt thereof using said insert, reservoir, nebulizer and/or inhaler to a patient, preferably an equine patient, more preferably a horse, in need thereof. Preferably the airway disease is a pulmonary disease, more preferably the airway disease is selected from the group consisting of: recurrent airway obstruction (RAO), summer pasture associated obstructive pulmonary disease (SPAOPD), and inflammatory airway disease (IAD).

The term "equine" means of or belonging to the family Equidae, which includes the horses, asses, and zebras, preferably horses. In addition, the term "equine" encompasses also hybrids of members of the family Equidae (e.g. mules, hinnies, etc.)

The term "patient" or "subject" embraces mammals such as primates including humans. The term "patient" or "subject" as used herein relates specifically to horses, especially horses suffering from airway disease (particularly pulmonary disease), preferably from recurrent airway obstruction (RAO) also called heaves or equine COPD and/or summer pasture associated obstructive pulmonary disease (SPAOPD) also called Summer Pasture Associated Recurrent Airway Obstruction (SPARAO) and/or inflammatory airway disease (IAD), most preferably from RAO.

The term "airway disease" in horses means the following: recurrent airway obstruction (RAO) also called heaves or equine COPD, Summer Pasture Associated Obstructive Pulmonary disease (SPAOPD), inflammatory airway disease (IAD), exercise induced pulmonary hemorrhage (EIPH), infectious diseases, chronic interstitial lung disease and upper respiratory tract functional disorders.

The term "pulmonary disease" means: recurrent airway obstruction (RAO) also called heaves or equine COPD, Summer Pasture Associated Obstructive Pulmonary disease (SPAOPD), inflammatory airway disease (IAD), exercise induced pulmonary hemorrhage (EIPH), infectious diseases, and chronic interstitial lung disease.

The term "recurrent airway obstruction (RAO)" in horses means the following: a chronic syndrome of mature horses with reversible airway obstruction in the stable showing periods of labored breathing at rest during exacerbation.

The term "Summer Pasture Associated Obstructive Pulmonary disease (SPAOPD)" in horses means the following: a chronic syndrome, which shares many clinical and pathological similarities with RAO at rest on the pasture, suggesting similar pathogenesis, however, it is caused by different antigens.

The term "inflammatory airway disease (IAD)" in horses means the following: a chronic syndrome of horses showing poor performance or coughing or excess tracheal mucus without showing periods of labored breathing at rest.

The term "effective amount" as used herein means an amount sufficient to achieve a reduction of airway disease in a horse when ciclesonide is administered at a dosage as described herein. The progress of the therapy (improvement of airway disease, particularly pulmonary disease, preferably recurrent airway obstruction (RAO) and/or Summer Pasture Associated Obstructive Pulmonary disease (SPAOPD) and/or inflammatory airway disease (IAD), most preferably RAO as described herein) can be monitored by standard airway/pulmonary diagnosis, for example, by clinical examination, airway fluid cytology, endoscopy, lung function measurement, or blood-gas analysis.

The term "pharmaceutically acceptable derivative thereof" means but is not limited to pharmaceutically acceptable salts, derivatives, metabolites or pro-drugs of a drug. Derivatives as used herein include but are not limited to, any hydrate forms, solvates, isomers, enantiomers, racemates, racemic conglomerate and the like of the compound of choice. Suitable pharmaceutically acceptable salts are well known in the art and may be formed with an inorganic or organic acid, such as hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

In a preferred aspect of the present invention the active substance administered using the insert, the reservoir, the nebulizer and/or the inhaler of the present invention is a glucocorticoid, preferably ciclesonide and/or budesonide and/or fluticasone, most preferably ciclesonide.

The term "glucocorticoid" refers to a class of steroid hormones that bind to the glucocorticoid receptor (GR), which is present in almost every vertebrate animal cell. The name glucocorticoid (glucose+cortex+steroid) derives from its role in the regulation of the metabolism of glucose, its synthesis in the adrenal cortex, and its steroidal structure.

Glucocorticoids are part of the feedback mechanism in the immune system that turns immune activity (inflammation) down. They are therefore used in medicine to treat diseases caused by an overactive immune system, such as allergies, asthma, autoimmune diseases, and sepsis.

Preferred glucocorticoids according to the present invention are ciclesonide and/or budesonide and/or fluticasone.

The term "ciclesonide" ((11β,16α)-16,17-[[(R)-Cyclohexylmethylene]bis(oxy)]-11-hydroxy-21-(2-methyl-1-oxopropoxy)pregna-1,4-diene-3,20-dione, $C_{32}H_{44}O_7$, $M_r$=540.7 g/mol) is well known in the art and means/ describes a glucocorticoid used to treat asthma and allergic rhinitis in humans. It is marketed for application in humans under the brand name Alvesco™ for asthma and Omnaris™/Omniair™ for hay fever in the US and Canada. Ciclesonide is a prodrug. It is transformed into the active metabolite C21-C21-desisobutyrylciclesonide (=desciclesonide) via hydrolysis by intracellular esterases in the lung. Ciclesonide is a non-halogenated glucocorticoid, which predominantly exists in its form as R-Enantiomer.

Formula III

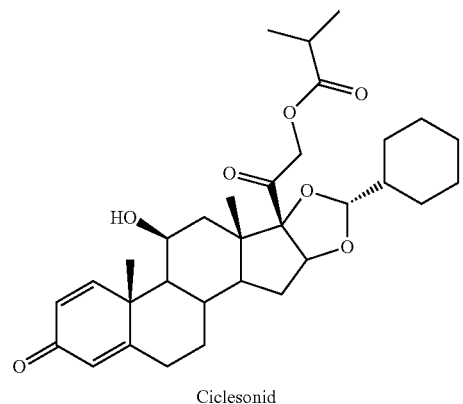

Ciclesonid

Formula IV

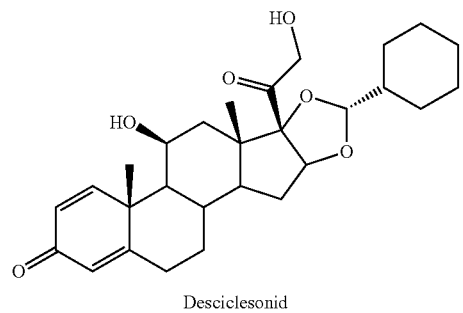

Desciclesonid

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound (also called the active metabolite), for example, by hydrolysis in blood or by activation via oxidation as in case of thioether groups. Most common prodrugs include esters and amide analogues of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can usually be readily prepared from the parent compounds using methods known in the art.

The medicament preparation according to the present invention preferably comprises the active substance or a pharmaceutically acceptable salt thereof. The medicament preparation preferably is a fluid or liquid, in particular comprising the active substance or the pharmaceutically acceptable salt thereof. The medicament preparation preferably comprises one or more solvents, in particular water, alcohol, ethanol or the like. The medicament preparation in particular is a solution and/or suspension from the active substance or a pharmaceutically acceptable salt thereof, in particular an aqueous, alcoholic, and/or ethanolic solution and/or suspension.

In a further aspect of the present invention, which can also be realized independently, an aerosol is produced with the insert, the reservoir, the nebulizer and/or the inhaler according to the present invention, from or with the medicament preparation comprising the active substance or a pharmaceutically acceptable salt thereof. It has been surprisingly shown that producing the aerosol and administering the aerosol is particularly efficient and effective in this case. In particular, the amount of the active substance or the pharmaceutically acceptable salt thereof that can be resorbed by a lung can be increased by means of the combination of the liquid medicament preparation comprising the active substance and the insert, the reservoir, the nebulizer and/or the inhaler for generating the aerosol with the medicament preparation, and preferably, the chamber forming a spacer, preferably with the respiratory orifice adapter.

The aspects mentioned above and described hereinafter can be implemented individually and in combination and also independently of one another. In particular, it is possible that the nebulizer, the nebulizer with the discharge nozzle, the nebulizer with the counter, the nebulizer with the discharge nozzle and the counter, the discharge nozzle with the activating device, the discharge nozzle with the activating device in conjunction with the nebulizer, the nebulizer with the inhaler, the discharge nozzle with the inhaler, and other combinations of the different aspects constitute independent inventions and are therefore implemented separately, independently of one another or in combination.

Further aspects, advantages and properties of the present invention will be apparent from the following description of preferred embodiments in conjunction with the accompanying drawings.

BRIEF DESCRIPTION OF THE DRAWINGS

FIG. 1 is a schematic perspective view of a reservoir with the proposed insert and a nebulized mounted thereon;

FIG. 2 is a side view of a proposed reservoir;

FIG. 3 is a schematic sectional view taken along the section line in FIG. 2;

FIG. 4 is a side view of the reservoir and nebulizer;

FIG. 5 is a schematic sectional view taken along the section line V-V in FIG. 4;

FIG. 6 is a perspective view of a proposed nebulizer;

FIG. 7 is another perspective view of a proposed nebulizer;

FIG. 8 is a perspective view of a counter;

FIG. 9 is a side view of the proposed nebulizer;

FIG. 10 is a schematic sectional view taken along the section line X-X in FIG. 9;

FIG. 11 is an enlarged view of encircled detail at the left of the proposed nebulizer in FIG. 10;

FIG. 12 is a an enlarged view of encircled detail of the discharge nozzle at the top in FIG. 10;

FIG. 12*a* is corresponding to that of FIG. 12, but showing a modified discharge nozzle;

FIG. 13 is a perspective view of a discharge nozzle according to a second embodiment;

FIG. 14 is a partial sectional view through the discharge nozzle according to the second embodiment of FIG. 13;

FIG. 15 is a perspective view of a discharge nozzle according to a third embodiment;

FIG. 16 is a side view of the discharge nozzle according to the third embodiment;

FIG. 17 is a sectional view of the discharge nozzle according to the third embodiment taken along the section line XVII-XVII in FIG. 16;

FIG. 18 is a sectional view of the discharge nozzle according to the third embodiment taken along the section line XVIII-XVIII in FIG. 16;

FIG. 19 is a perspective view of a discharge nozzle according to a fourth embodiment;

FIG. 20 is a side view of the discharge nozzle according to the fourth embodiment of FIG. 19;

FIG. 21 is a sectional view of the discharge nozzle according to the fourth embodiment taken along the section line XXI-XXI in FIG. 20;

FIG. 22 is a sectional view of the discharge nozzle according to the fourth embodiment taken along the section line XXII-XXII in FIG. 20;

FIG. 23 is a perspective view of a discharge nozzle according to a fifth embodiment;

FIG. 24 is a side view of the discharge nozzle according to the fifth embodiment;

FIG. 25 is a sectional view of the discharge nozzle according to the fifth embodiment taken along the section line XXV-XXV in FIG. 24;

FIG. 26 is a sectional view of the discharge nozzle according to the fifth embodiment taken along the section line XXVI-XXVI of FIG. 24;

FIG. 27 is a schematic side view of a proposed inhaler in use;

FIG. 28 is a schematic sectional view of the proposed inhaler taken along the section line XXVIII-XXVIII in FIG. 27 with the insert inserted; and FIG. 29 is a schematic sectional view of the proposed inhaler taken along the section line XXVIII-XXVIII in FIG. 27 but without an insert.

DETAILED DESCRIPTION OF THE INVENTION

In the following, the same reference numerals have been used for identical or similar parts where identical or similar properties and advantages can be achieved, even if the relevant description has not been repeated.

FIG. 1 shows, in perspective view, a proposed insert 1 on a reservoir 2.

FIGS. 2 & 3 show the reservoir 2 which is preferably configured to hold a medicament preparation 3. The medicament preparation 3 is preferably a liquid, particularly a solution and/or suspension 3 which is held under pressure. For this purpose the reservoir 2 may comprise or contain propellant 4, such as propellant gas. Alternatively or additionally, the medicament preparation 3 may contain the propellant 4. The reservoir 2 may be at least partly filled or fillable with a mixture of medicament preparation 3 and propellant 4.

The reservoir 2 preferably forms an inner space sealed off in pressure-tight manner for receiving the preferably pressurized medicament preparation 3.

The reservoir 2 has a wall 6. The wall 6 forms a container with an opening 7 which is preferably closed off, particularly in a gastight manner. In the embodiment shown, the opening 7 is closed off by a lid, normally referred to as a valve plate 8, or by some other closure means into which a valve 9 is preferably insertable or inserted. However, other solutions are also possible here.

The reservoir 2 preferably comprises the valve 9. Particularly preferably, the valve 9 is arranged in the lid or valve plate 8. The valve 9 may be received or held by the valve plate 8 or the other closure means. In particular, the valve 9 is sealingly mounted, for example, pressed into the valve plate 8 or sealingly held therein in some other way.

The valve 9 is preferably a metering valve. A metering valve may be configured to dispense a certain quantity or dose when actuated. A metering valve is thus particularly configured not to provide a continuous fluid connection between the inlet and outlet Preferably, when the valve 9 is actuated, a fluid connection from a dispensing opening 13 of the valve 9 is established only with a metering chamber 10 of the valve and/or is not continuously formed with the inner space 5 of the reservoir 2.

The valve 9 may comprise a valve element 11. The valve 9 is preferably embodied to be opened and closed by the movement of the valve element 11. For this purpose, the valve element 11 may be inclined or rotated. Particularly preferably, the valve 9 is embodied to be opened or closed, respectively, by an axial or vertical movement of the valve element 11.

The valve element 11 is preferably biased toward the closed position. The valve 9 may be a self-closing valve, in this way or by other means. In particular, the valve element 11 is biased into the closed position and can be moved counter to the bias, thereby opening the valve 9.

The valve 9 may be male or female. Preferably, the valve element 11 allows axial flow, thus enabling a fluid connection to be formed for the dispensing of the medicament preparation 3 through the valve element 11. However, other solutions are also possible.

In the embodiment shown, the valve element 11 preferably comprises a valve stem 12. The valve stem 12 may be integrally formed with the valve element 11, pushed into the valve element 11 or otherwise attached to the valve element 11.

The valve stem 12 preferably projects beyond the valve plate 8 and is able to actuate the valve 9 by axial movement. Alternatively or additionally, however, the valve 9 may also be embodied as a female valve. For this purpose, the valve 9 may have an opening into which a valve stem 12 by means of which the valve 9 can be actuated can be pushed from outside. However, other solutions are also possible.

The valve element 11 is preferably configured so as to produce a fluidic connection between the metering chamber 10 and the dispensing opening 13 preferably formed by the valve stem 12, particularly by axial movement.

The valve element 11 may also be configured to connect the metering chamber 10 fluidically to the inner space 5 of the reservoir 2. It is particularly preferred if the movement of the valve element 11 can produce either a fluid connection between the inner space 5 of the reservoir 2 and the metering chamber 10 or a fluid connection between the dispensing opening 13 and metering chamber 10, but preferably not at the same time.

In the embodiment shown, the valve element 11 may comprise a collar 14 which is biased against a seal or sealing surface 15. In this way the valve 9 can be closed or can block dispensing of the medicament preparation 3 from the inner space 5.

Moreover, the valve stem 12 may have a lateral orifice 16. The lateral orifice 16 is preferably fluidically connected to the dispensing opening 13. The orifice 16 may be arranged, in a closed state of the valve 9, on a side of the sealing surface 15 remote from the metering chamber 10. This provides ventilation.

On a side remote from the dispensing opening 13, the valve element 11 may have a sealing region 17. The sealing region 17 may be configured so as to correspond to the valve element 11. In particular, the sealing region 17 is arranged and configured such that an axial movement of the valve element 11 can block a fluid connection between the inner space 5 and the metering chamber 10.

For actuating or activating the dispensing of the medicament preparation 3, the valve element 11 may be axially moveable, while an existing fluid connection between the inner space 5 and the metering chamber 10 is preferably closed off at the sealing region 17, particularly relative to a valve housing 18 or an entry seal 19 arranged there. As the movement continues, the orifice 16 reaches the side of the sealing surface 15 which faces the metering chamber 10 and provides a fluid connection between the metering chamber 10 and the dispensing opening 13. However, other solutions are also possible.

The valve element 11 is preferably biased into the direction of closing by a spring 20. In the closed position of the valve 9, the valve is closed or a fluid connection between the metering chamber 10 and the dispensing opening 13 is blocked. At the same time, a fluid connection may be formed between the metering chamber 10 and the inner space 5. However, other solutions are also possible.

The reservoir 2 preferably comprises an immersion tube 21 or is otherwise embodied so as to be operated by the valve 9 which is preferably directed upwards in the position of use.

Figure 27:
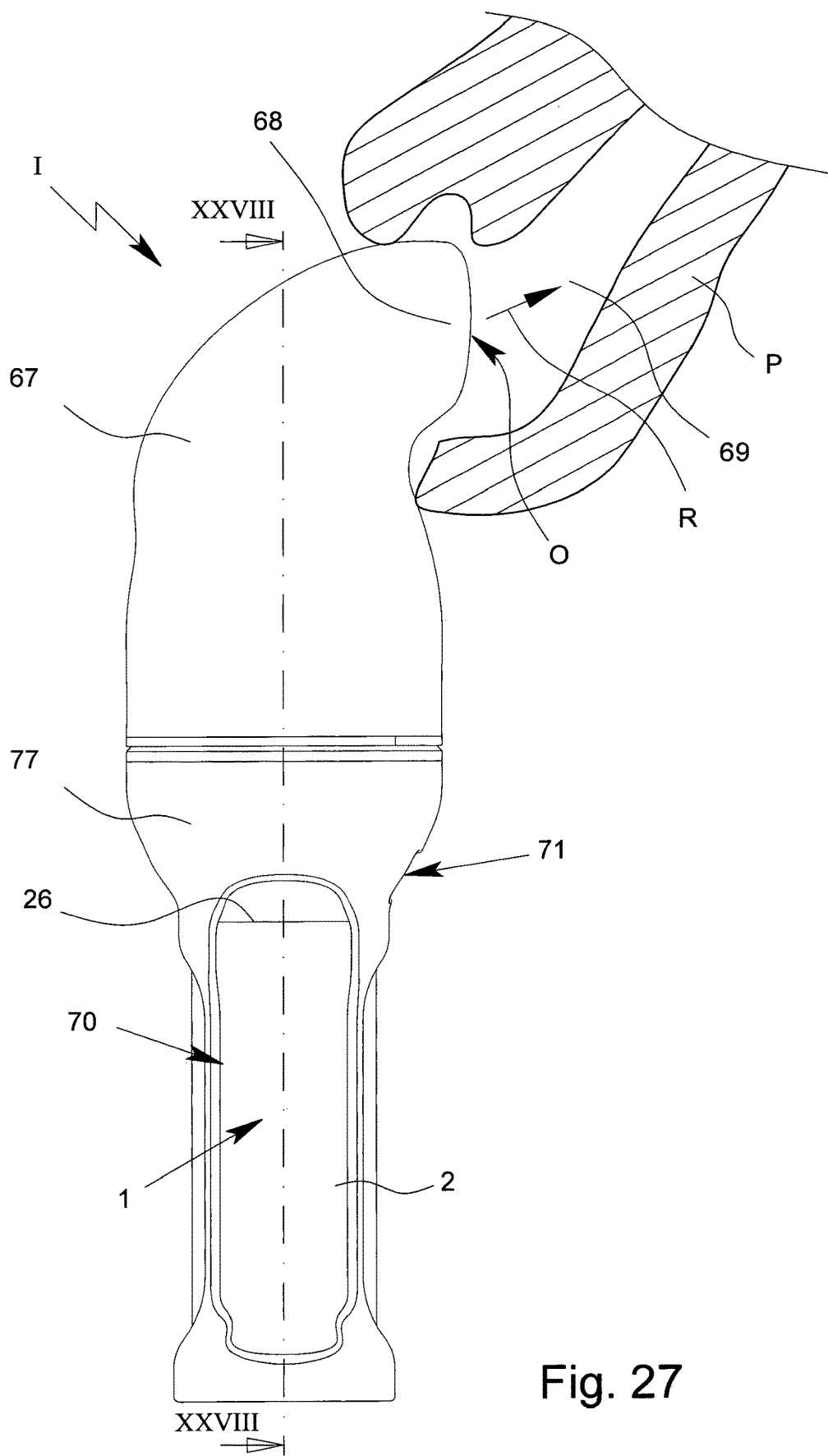

The position of use is particularly characterized in that an inhaler I with the insert 1 can be inserted in a respiratory orifice of a living creature so that the medicament preparation 3 can be administered as shown in FIG. 27, for example. The position of use may relate to the insert 1, even if it has not been inserted in the inhaler I. In this case, it is preferable for the position of use to denote an alignment of the insert 1 which the insert 1 would assume within the inhaler I. Alternatively or additionally, the valve 9 in the position of use faces away from the ground. In particular, the position of use of the insert 1 is upright or an upright position. For this purpose, the valve 9 may be turned upwards.

In the embodiment shown the valve 9 is connected with the inlet end of the immersion tube 21 such that an intake opening 22 of the immersion tube 21 is provided in the base region 23 of the reservoir 2. However, other solutions are also possible, in particular without an immersion tube 21.

In an alternative (not shown), the medicament preparation 3 may be arranged in a pouch. The pouch is preferably arranged in the reservoir 2 and forms an inner space which is connected to the valve 9. In this case, the propellant 4 may surround the pouch. In such a solution, operation independent of position may be possible.

However, it is particularly preferred if at least upright operation or dispensing of the medicament preparation 3 is possible with the valve 9 facing upwards in the position of use.

Figure 3:
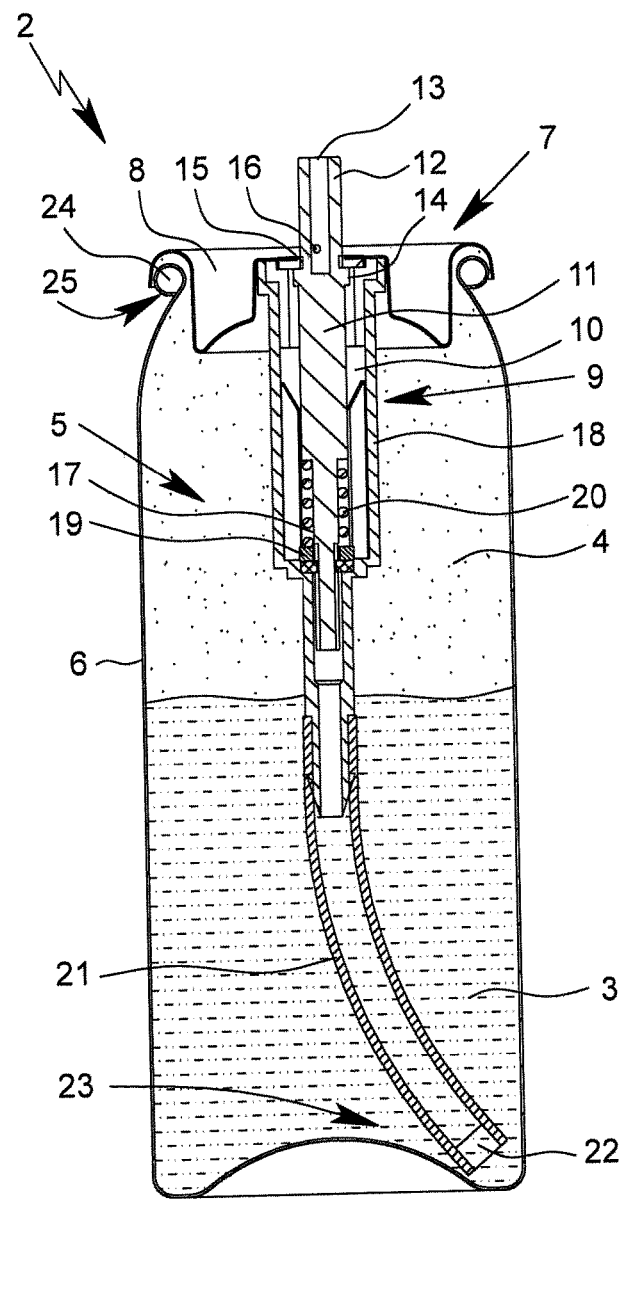
Figure 4:
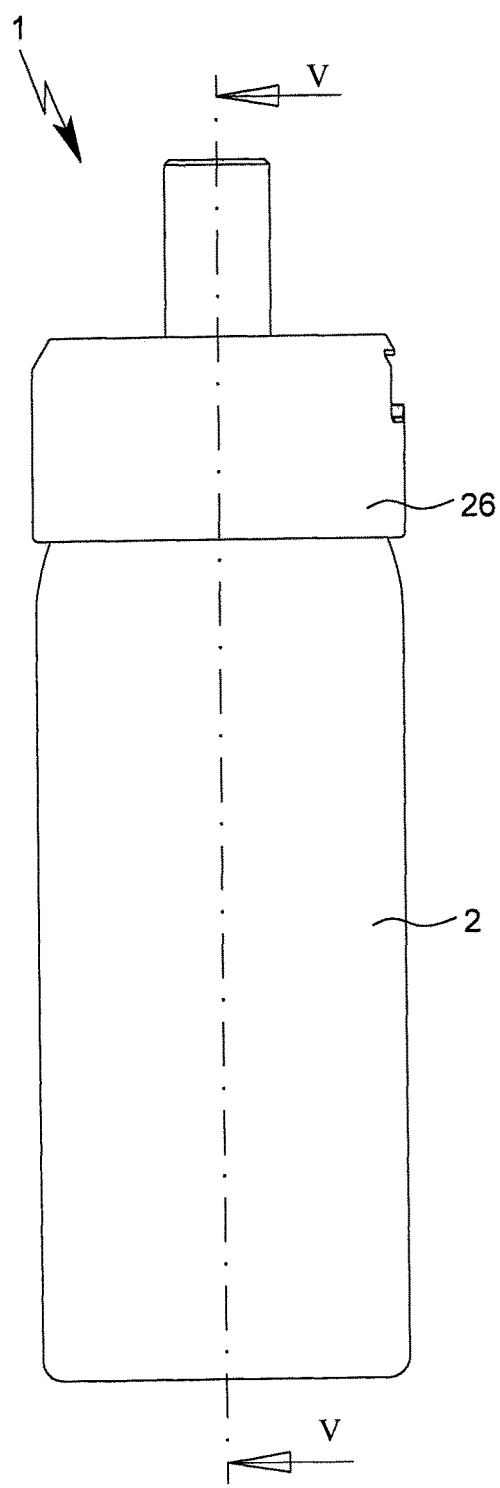

In the embodiment according to FIG. 3, the reservoir 2 is closed off by the valve plate 8 or other closure means. In particularly, the valve plate 8 or closure is flanged with the wall 6 of the reservoir 2. The reservoir 2 may have a flanged or crimped edge 24 on the valve side. The crimped edge 24 may form an undercut 25. The undercut 25 is shown as being circumferential in the embodiment shown. However, the undercut 25 may also be formed in some other way than by a crimped edge or may be only partially circumferential or non-circumferential in some other way.

FIG. 4 shows a side view of the proposed insert 1 in which a nebulizer 26 is preferably arranged or mounted on the reservoir 2 on the valve side.

FIG. 5 shows a section through the insert of FIG. 4 along section line V-V. The reservoir 2 corresponds to the reservoir 2 described in conjunction with FIGS. 2 and 3, and for this reason, reference may be made to the previous remarks.

The nebulizer 26 is mounted on the reservoir 2 or held directly on reservoir 2 by some other method. In the embodiment shown, the nebulizer 26 comprises a latching surface 27 which can engage in the undercut 25. The surface latching 27 may be formed, for example, by one or more latching projections. Preferably, an at least substantially continuous and/or circumferential latching surface 27 is used, particularly a bead, a projection or the like. This promotes non-removable holding of the nebulizer 26 on the reservoir 2. The nebulizer 26 may be secured by latching to the reservoir 2 by this or other means.

Alternatively or additionally, the nebulizer 26 may be attached or held on the reservoir 2, particularly on the wall 6 or crimped edged 24, by adhesion, clamping, clipping, injection molding or some other method, preferably with interlocking engagement. However, it is also possible for the nebulizer 26 to be rotationally fixed or held on the reservoir 2.

Preferably, the nebulizer 26 is permanently held on or connected to the reservoir 2. The nebulizer 26 may form a construction unit with the reservoir 2. In particular, the nebulizer 26 forms an inseparable construction unit with the reservoir 2. A construction unit is inseparable particularly when essential components cannot be separated from one another without being damaged or destroyed. The nebulizer 26 is thus attached to the reservoir 2, in particular, such that total separation of the nebulizer 26 from the reservoir 2 leads to damage or destruction of the nebulizer 26 or in some other way renders the insert 1 unusable.

The nebulizer 26 may also be produced and operated independently of the reservoir 2 or an inhaler I. A separate nebulizer 26 of this kind may, for example, be made available separately as a semi-finished product to a manufacturer or filler of the reservoirs 2. A separate nebulizer 26 is preferably inseparable and/or can only be connected to a reservoir 2 once, particularly can be clipped to the reservoir 2. However, other solutions are also possible.

A discharge nozzle 28 is associated with the nebulizer 26. Preferably, the nebulizer 26 comprises the discharge nozzle 28, accommodates it or retains it. The discharge nozzle 28 is preferably embodied so as to dispense the medicament preparation 3 and/or to form an aerosol 29 with the medicament preparation 3.

The discharge nozzle 28 is preferably fluidically connected to the valve 9. In particular, the discharge nozzle 28 is connected to the valve element 11 or the valve stem 12. Preferably, the discharge nozzle 28 can move the valve element 11 and thus open the valve 9. However, other solutions are also possible.

It is preferable if the discharge nozzle 28 is mounted in the nebulizer 26 to be axially moveable at least to a limited extent and in particular is mounted to be connected or fixed for rotation. The nebulizer 26 is thus preferably configured to allow axial movement of the discharge nozzle 28. In addition, the nebulizer 26 is preferably embodied to prevent rotation and removal of the discharge nozzle 28, particularly to block it by positive engagement.

It may be sufficient if the discharge nozzle 28 is not removable when the insert 1 has been installed or the nebulizer 26 is attached to the reservoir 2. Axial movement or removal of the discharge nozzle 28 from the nebulizer 26 may be blocked in the direction of the reservoir 2 by the reservoir 2, itself.

The discharge nozzle 28 preferably comprises a nozzle body 30. The nozzle body 30 may comprise a fluid channel 31 for fluidically connecting the dispensing opening 13 of the valve 9 to the environment.

The activating element 32 is arranged around the nozzle body 30 in the embodiment shown and/or is at least substantially annular. The activating element 32 may, however, be of asymmetric construction, particularly oval, bone-shaped or provided with protrusions, projections or the like, particularly in section at right angles to a central axis of the nozzle body 30 or the channel 31. These or other means may ensure that the activating element 32 can perform an axial movement, but not a rotary or turning movement.

The activating element 32 is preferably secured against rotation. Moreover, the activating element 32 preferably secures the discharge nozzle 26 or the nozzle body 30 against rotation.

The activating element 32 can accommodate and/or hold the nozzle body 30, particularly by interlocking and/or frictional engagement. In particular, the nozzle body 30 is fixedly connected, pressed, adhesively bonded or formed in one piece with the activating element 32. The activating element 32 may block or prevent movement or removal of the nozzle body 30 in a direction A for the aerosol 29.

The activating element 32 may be or form part of the nozzle body 30 or the discharge nozzle 28. In the embodiment shown, the activating element 32 forms a shoulder of the nozzle body 30 or the discharge nozzle 28. The activating element 32 may, however, also be formed in a different manner and/or independently of the discharge nozzle 28 or the nozzle body 30.

The activating element 32 is preferably configured so as to allow activation of the dispensing of the medicament preparation 3. For this purpose, the activating element 32 may interact with the valve 9 or act upon the valve 9. Particularly preferably, the activating element 32 is embodied to move the valve element 11 axially, in particular, and thereby open the valve 9 or actuate the dispensing of the medicament preparation 3.

In a variant which is not shown in detail, the activating element 32 is produced and/or moveable separately from the discharge nozzle 28 or the nozzle body 30. In this case too, it is particularly preferable if the activating element 32 is embodied to move the valve element 11, to open the valve 9 or to dispense the medicament preparation 3. It is thus possible for the activating element 32 to actuate the valve without moving the nozzle body 30 or the discharge nozzle 28.

In one variant, it is possible for the valve element 11 or the valve stem 12 to be moveable within the nozzle body 30 in the manner of a piston. In this way or otherwise, the nozzle body 30 or the discharge nozzle 28 may, in particular, be removable relative to the reservoir 2 during the opening of the valve.

The activating element 32 may move the valve stem 12 and/or the valve element 11 without the discharge nozzle 28 or the nozzle body 30 having to be moved.

Preferably, however, the activating element 32 forms a construction unit or fixed composite with the discharge nozzle 28. This has proved to be a particularly robust, simple and inexpensive solution.

The activating element 32 is preferably protected from accidental actuation by a frame or a shoulder S. In particular, the frame or the shoulder S is arranged adjacent to the activating element 32, projects relative to the activating element 32 and/or surrounds the activating element 32, preferably in the manner of a frame or shoulder.

The nebulizer 26 preferably comprises a housing 33 which may form the engagement surface 27 or may be attached to the reservoir 2 or the wall 6 thereof.

The frame or the shoulder S is/are preferably formed by the housing 33 or is/are attached to the housing 33 or otherwise rendered immovable relative to the reservoir 2. This prevents accidental manual movement of the activating element 32 and consequent possible triggering of the dispensing of the medicament preparation 3.

Preferably, the discharge nozzle 28, the nozzle body 30 or the activating element 32 is or are arranged on or at least partially in the housing 33.

The discharge nozzle 28 and/or the nozzle body 30 and/or the activating element 32 are preferably held in or on the housing in non-removable manner, preferably by interlocking engagement. However, at least axial movement of the activating element 32, the nozzle body 30 or the discharge nozzle 28 on or in the housing 33 is preferably provided, particularly for actuating the valve 9 or moving the valve element 11.

In addition, the nebulizer 26 may comprise a counter 34. The counter 34 is preferably configured to be driven by initiating the dispensing of the medicament preparation 3. In particular, the counter 34 can be driven by the axial movement of the activating element 32, the nozzle body 30 and/or the discharge nozzle 28.

Figure 6:
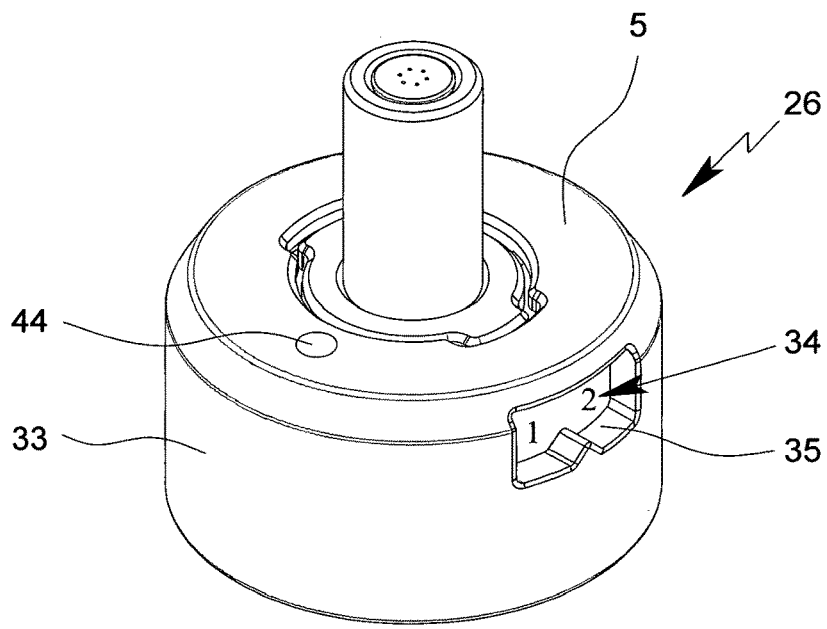
Figure 7:
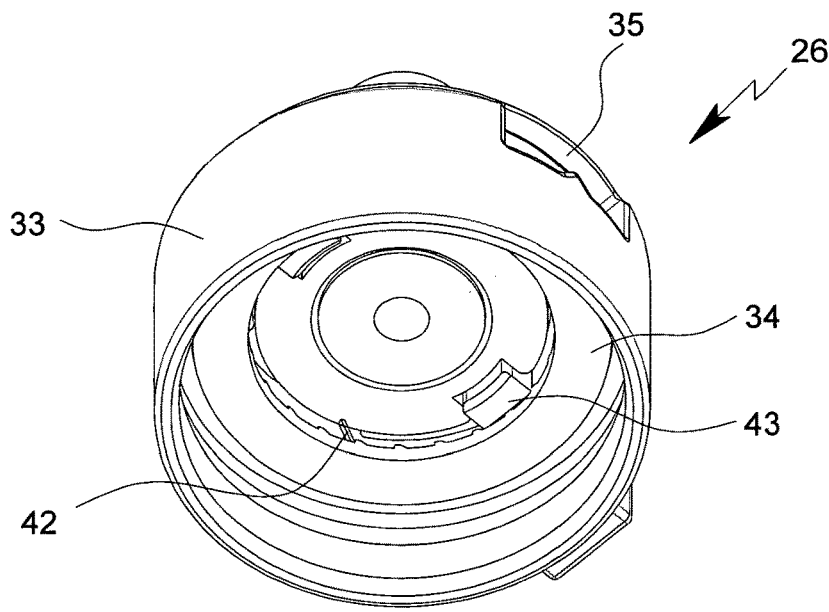
Figure 8:
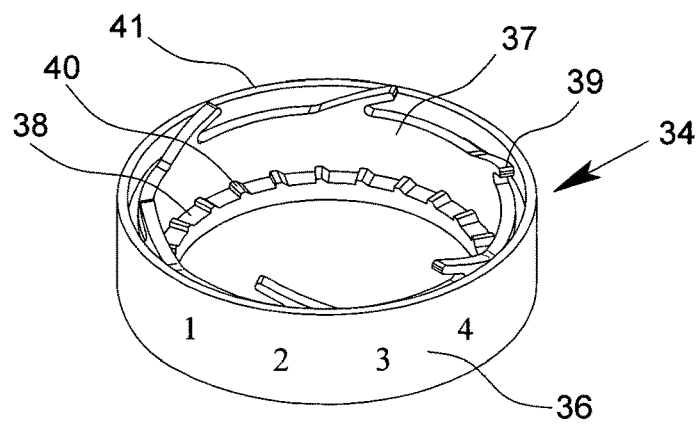
Figure 13:
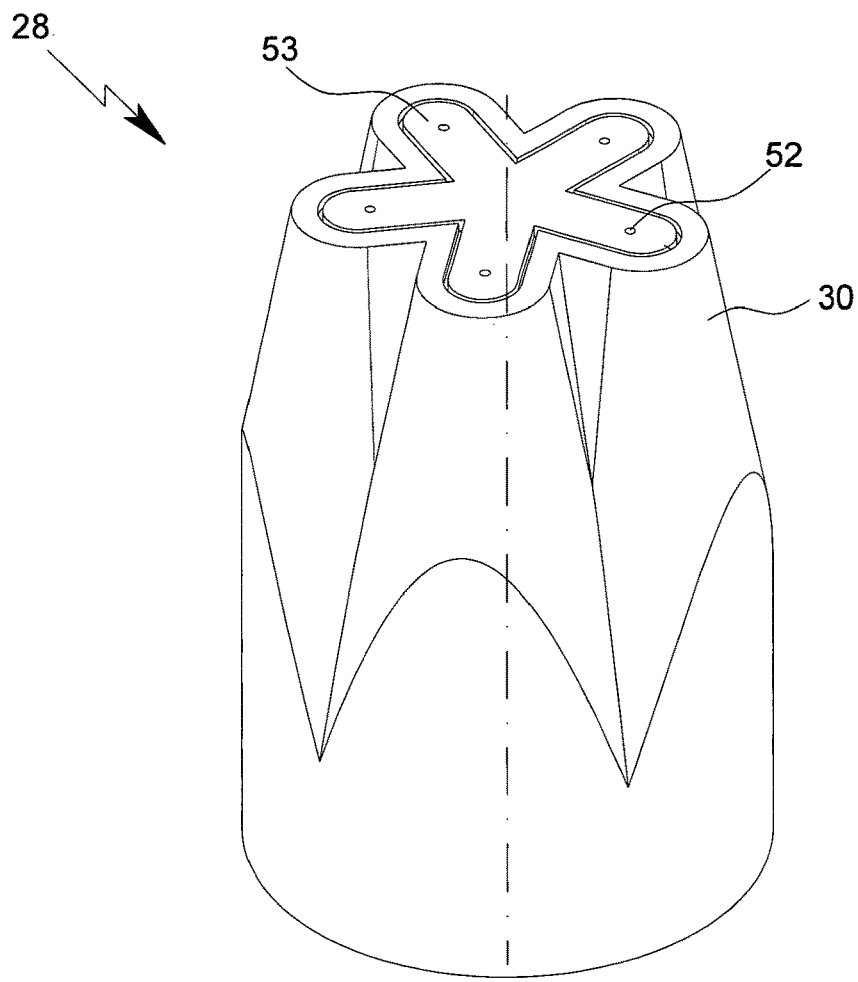
Figure 14:
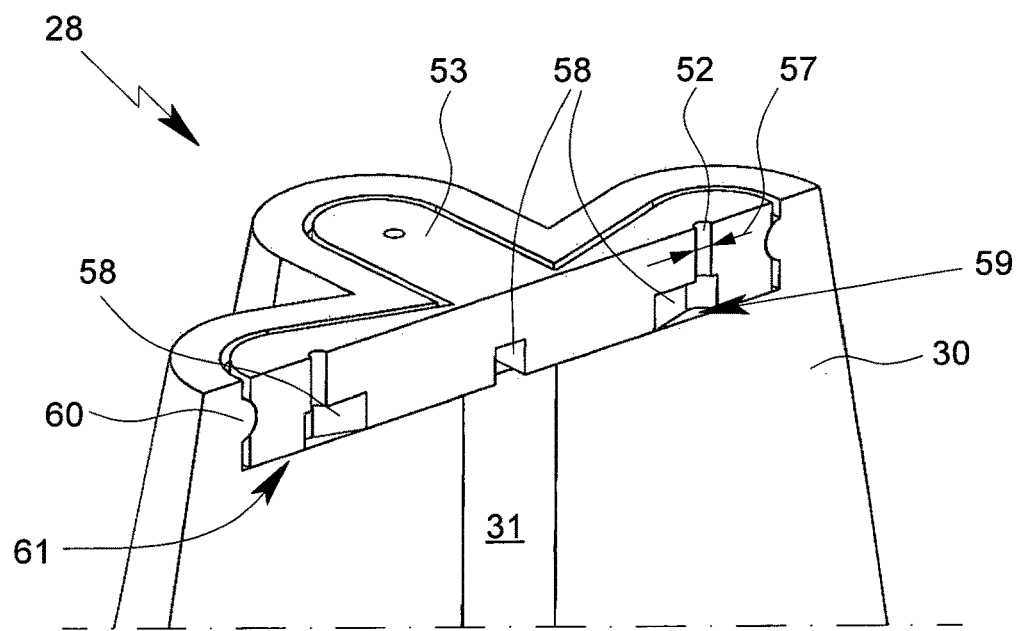

The nebulizer 26 is hereinafter described in more detail by reference to FIGS. 6 to 8, where FIG. 6 shows a perspective view of the nebulizer 26 from diagonally above, FIG. 7 is a perspective view of the nebulizer 26 from diagonally below and FIG. 8 is a perspective view of the counter 34 which is preferably inserted or insertable in nebulizer 26.

The housing 33 may comprise a window 35 to which the counter 34 is visible from outside. In the embodiment shown, the window 35 is provided as an orifice in the housing 33. However, the counter 34 may also be visible from outside in some other way. In FIG. 7, the counter 34 is inserted in the nebulizer 26.

In the embodiment shown in FIG. 8, the counter 34 is at least substantially annular and/or rotatable in configuration.

The counter 34 may comprise a display device 36, particularly a scale or the like. This is preferably provided on the radially outer edge or on a radially outer or circumferential surface of the counter 34. However, other solutions are also possible.

For example, the display device 36 may alternatively or additionally be provided axially, at the end face or on other parts of the counter 34. Arrangement on a radially outer and preferably circumferential surface has the advantage that the counter 34 is easily visibly from outside after the insertion of the proposed insert 1 in a corresponding inhaler I, for example, by means of corresponding windows, orifices or openings.

The counter 34 preferably comprises a return preventer means 37 and/or a driver 38.

The return preventer means 37 is preferably designed to allow the counter 34 to be moved only in one direction and to block it in any other or opposite direction, e.g., in the manner of a ratchet mechanism. With a counter 34 of at least substantially annular construction, the return preventer means 37 may thus be embodied to allow rotation only in one direction and to block it in another direction.

The driver 38 is preferably configured to move the counter 34, particularly to rotate it.

The return preventer means 37 and the driver 38 preferably cooperate such that the counter 34 is drivable, particularly rotatable. For this purpose, the driver 38 may cause the counter 34 to rotate in one direction and the return preventer means 37 may prevent it from turning back. In this way, the counter 34 may be moveable, particularly rotatable, in only one direction.

The counter 34 may comprise one or more flexible strips 39 which are mounted or molded on the counter 34 or preferably integrally formed with the counter by some other method.

The flexible strips 39 may act as springs. The strips 39 may enable the counter 34 to be seated securely in the nebulizer 26.

Alternatively or additionally, the flexible strips 39 may prevent rotation of the counter 34 in one direction and/or permit it only in one direction in the manner of a ratchet. In this way the return preventer means 37 may be formed with the flexible strips 39.

The counter 34 is preferably drivable by actuation of the dispensing of the medicament preparation 3.

The driver 38 preferably comprises drive means 40, particularly teeth or pawls. In the embodiment shown in FIG. 8 the flexible strips 39 are embodied as a gear ring. However, other solutions are also possible.

It is preferable if the counter 34, particularly the return preventer means 37 and/or the driver 38 interact with the housing 33, with the activating element 32, with the nozzle body 30 and/or with the discharge nozzle 28 so that by axial movement of the activating element 32 the counter 34 can be driven, particularly rotated.

The return preventer means 37 of the counter 34 preferably engages on a surface of the nebulizer 26, particularly of the housing 33, in the position of use, so that movement of the counter 34 is blocked in one direction, particularly a direction of rotation, preferably by interlocking and/or frictional engagement.

The counter 34 may comprise guide means to enable a guided rotary movement of the counter 34 in the housing 33 of the nebulizer 26. In the embodiment shown in FIG. 8, a ring 41 is provided which serves as guide means and may form or carry the display device 36.

Preferably, the nebulizer 26 comprises a counter drive 42. The counter drive 42 may be configured to cause advance of the counter 34, particularly rotation thereof, by axial movement of the activating element 32, the discharge nozzle 28 or the nozzle body 30.

The counter drive 42 is preferably arranged or fixed on the activating element 32 or formed in one piece with the activating element 32.

In the embodiment according to the FIG. 7, the counter drive 42 is formed by a flexible strip, a spring arm, a lever or the like.

The counter drive 42 may be altered by axial movement of the activating element 32 or of the nozzle body 30 in its angle relative to the activating element 32, or extended, for example, by deformation. In this way, axial movement of the activating element 32, nozzle body 30 or the discharge nozzle 28 may be converted into rotary movement of the counter 34. However, again other drive concepts are possible.

In the embodiment according FIG. 7, the activating element 32 or the discharge nozzle 28 or the nozzle body 30 is guided by a guide 43 axially and/or connected for rotation or to prevent accidental rotation.

The guide 43 may alternatively or additionally also be slightly helical in configuration. In one embodiment it is possible for the activating element 32 to be rotated by a guide 43 during axial movement. This enables the activating element 32 or discharge nozzle 28 to be rotated as they move axially. The counter drive 42 may transmit a rotary movement of this kind to the counter 34.

The counter drive 42 may comprise a follower or be embodied as a follower. In this way, a rotary movement of the activating element 32 or of the discharge nozzle 28 or nozzle body 30 may be used to drive the counter 34.

For driving the counter 34, the counter drive 42 may engage in the drive means 40 of the counter 34, particularly in a latching engagement or in the manner of a ratchet. The return preventer means 37 and the driver 38 may thus be or comprise ratchets rotating in opposition directions, in particular.

When the activating element 32 is moved in order to activate the dispensing of the medicament preparation 3, the counter 34 may be moved in a first direction and, when the activating element 32 is moved back into its starting position, a contrary rotary movement of the counter 34 can be prevented by the return preventer 37. The counter drive 42 may slide over a pall of the drive means 40 and when the activating element 32 is next moved to activate the dispensing of the medicament preparation 3, it may be engage in a next or adjacent detent of the drive means 40. In this way, it is possible to achieve a driving movement of the counter 34 in one direction.

FIG. 9 shows a side view of the proposed nebulizer 26 and FIG. 10 shows a section through the nebulizer 26 on the section line X-X in FIG. 9.

The dispensing of the medicament preparation 3 from the reservoir 2 can be achieved by actuating the valve 9. For this purpose, as already described in connection with FIG. 3, the valve element 11 is preferably moved axially. In particular, the valve stem 12 is pressed in the direction of the reservoir 2, as a result of which the valve element 11 is able to produce a fluidic connection between the metering chamber 10 and the dispensing opening 13.

The valve element 11 is preferably moveable by the activating element 32 or the nozzle body 30 or the discharge nozzle 28.

The discharge nozzle 28 or nozzle body 30 preferably has a valve connector 48 for connecting to the valve element 11 or valve stem 12.

Figure 5:
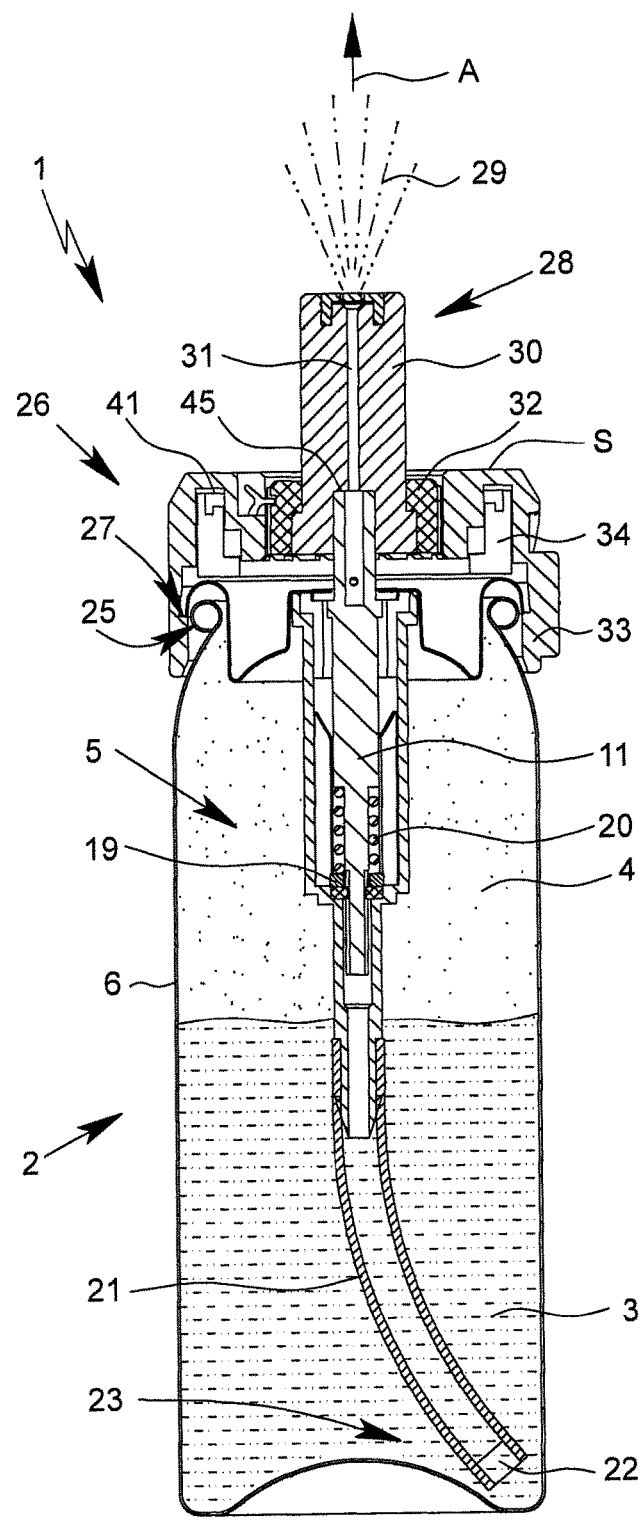

In the embodiment shown in FIG. 5, the valve stem 12 or the valve element 11 is sealingly accommodated in the valve connector 48 and/or held by the valve connector 48.

The valve connector 48 may comprise a stop 49, particularly an annular shoulder, for the valve element 11 or valve stem 12. In this way the valve element 11 or the valve stem 12 can be moved by the movement of the discharge nozzle 28, the nozzle body 30 or the activating element 32.

The dispensing of the medicament preparation 3 can be initiated by a preferably axial movement of the valve element 11 or valve stem 12. The medicament preparation 3 contained in the metering chamber 10 is preferably pressurized and is forced by this excess pressure through the channel 31 in the nozzle body 30. As a result the medicament preparation 3 can be dispensed and the aerosol 29 formed.

The insert 1 or nebulizer 26 preferably comprises a blocking device 44. The blocking device 44 is preferably configured to prevent initiation of the dispensing of the medicament preparation 3, particularly to block and/or allow or release this dispensing.

In particular, the blocking device 44 is configured to prevent the dispensing of the medicament preparation 3 if the insert 1 had not been inserted, or at least not fully inserted, into a corresponding inhaler I or is not in its position of use for some other reason.

Alternatively or additionally, the blocking device 44 is configured for this purpose and/or to allow the dispensing of the medicament preparation 3 when the insert 1 has been inserted in a corresponding inhaler I, preferably oriented and/or completely. The blocking device 44 may block or allow a preferably axial movement of the discharge nozzle 28, the nozzle body 30 and/or the activating element and/or a movement of the valve element 11. However, other solutions are also possible for preventing or allowing the dispensing of the medicament preparation 3, for example, by means of an additional valve or the like.

FIG. 11 shows a magnified detail of the region of the blocking device 44 from FIG. 10.

The blocking device 44 may comprise an interlocking element 45 which is able to engage in the activating element 32, particularly in a locking portion 47 of the activating element 32, for example, a recess in the activating element 32. In this way, or by other means, it is possible to prevent the activating element 32 or the nozzle body 30 or the discharge nozzle 28 from being moved axially, in particular.

The nozzle body 30 or the nozzle recess 32 or the discharge nozzle 28 is/are therefore preferably capable of being blocked axially by the blocking device 44. In this way, actuation of the valve 9 and discharge of the medicament preparation 3 can be prevented.

The blocking device 44 is preferably configured so that dispensing of the medicament preparation 3 is prevented outside an inhaler I or until the insert 1 has been inserted in a corresponding inhaler I or has reached its position of use.

The blocking device 44 may be required for safety purposes. Advantageously, the blocking device 44 makes it possible to prevent the formation of aerosol outside the inhaler I. The concentration of active substances in the medicament preparation 3 may be high, particularly if the insert 1 or the inhaler I is intended for use in large animal. Accidental actuation and breathing in of the aerosol 29 may therefore have serious consequences. The proposed blocking device 44 prevents accidental actuation outside the inhaler I.

The blocking device 44 may be at least partially bendable, flexible and/or deformable. The blocking device 44 is preferably configured to trigger release, irreversibly, preferably by separation or destruction, or reversibly, particularly by sliding or bending.

In the embodiment shown in FIG. 10, the blocking device 44 has a sloping surface 46. The sloping surface 46 may be configured to initiate locking by means of the interlocking element 45. For this purpose, a force F may act on the sloping surface 46, thereby bending the blocking device 44 or in some other way moving it out of engagement with the locking portion 47. In this way, the blocking device 44 may allow activation of the dispensing of the medicament preparation 3.

The release by the blocking device 44 is preferably produced by the inhaler I on the blocking device 44 during the insertion of the insert 1 or the nebulizer 26 into the inhaler I.

In alternative embodiments of the blocking device 44, not shown here, a rod or bolt may be provided which is in engagement with the discharge nozzle 28, the nozzle body 30 or the activating element 32 or in some other way blocks or prevents movement of the discharge nozzle 28, the nozzle body 30 and/or the activating element 32. In this way, it is possible to prevent activation of the dispensing of the medicament preparation 3. The bolt or rod may be movable, particularly slidable thus freeing up the activation of the dispensing of the medicament preparation 3. However, other solutions are also possible.

In an alternative embodiment which is also not shown here, the blocking device 44 may comprise an element having a frangible point which may be mounted on, adhered to, molded on or formed in one piece with the discharge nozzle 28, the nozzle body 30 and/or the activating element 32. The element is preferably configured to be destructible or separable when the insert 1 is inserted into an inhaler I. This prevents activation outside the inhaler I and/or allows activation by the insertion of the insert 1 into the inhaler I.

In general, the blocking device 44 may prevent actuation of the valve 9 in an initial state or delivery state or allow it only after insertion into a corresponding inhaler I. The dispensing of the medicament preparation 3 can be permitted by the blocking device 44, particularly by preferably fully inserting the insert 1 into the inhaler I, as will be discussed in more detail hereinafter in connection with the description of the inhaler I from FIGS. 27-29.

In an alternative embodiment (not shown) the insert 1, particularly the blocking device 44, can prevent actuation of the dispensing of the medicament preparation 3 after a given number of actuating processes has been reached or exceeded. For this purpose, preferably and in particular, axial movement of the valve element 11, the discharge nozzle 28, the nozzle body 30 and/or the activating element 32 is prevented or blocked as soon as the predetermined number of actuation processes is reached or exceeded.

The counter 34 may be arranged so as to prevent further activation or further, in particular, axial movements of the valve element 11 or valve stem 12 after the predetermined number of actuation processes has been reached or exceeded, preferably counted by the counter 34. This can be achieved by the fact that the counter 34 acts on the blocking device 44 so that the latter prevents movement of the discharge nozzle 28, the nozzle body 30 and/or the activating element 32.

Alternatively or additionally, the counter 34 may prevent further, particularly axial, movement of the discharge nozzle, the nozzle body 30 and/or the activating element 32 directly, preferably by interlocking engagement, by means of interlocking engagement means or other blocking means provided on the counter 34, or may otherwise prevent actuation of the valve 9. However, other solutions are also possible.

The insert 1 or the nebulizer 26 preferably comprise or comprises an orientation device, particularly an orientation projection 50, for example, a lug, tab or the like and/or an orientation recess 51.

The nebulizer 26 or the insert 1 may comprise one or more orientation devices for securing the orientation, particularly the rotary orientation or rotary position, of the nebulizer 26 or insert 1.

The orientation device is preferably configured to allow total insertion or the reaching of a position of use of the insert 1 or the nebulizer 26 in only one specific rotary position of the nebulizer 26 or insert 1, by corresponding means, and to prevent them in other rotary positions of the insert 1 or nebulizer 26.

By means of the orientation projection and recess 50, 51, the insert 1 can be inserted, placed or pushed into the inhaler I only in a specific position, rotary position and/or orientation of the insert 1 of nebulizer 26.

Alternatively or additionally, the orientation projection and recess 50, 51 are configured to allow actuation of the dispensing of the medicament preparation 3 only in the specified position, rotary position and/or orientation of the insert 1 or nebulizer 26.

Preferably, insertion of the insert 1 or nebulizer 26 into the inhaler I is blocked in one or more rotary positions and enabled in one or more rotary positions. In this way, a position, alignment and/or rotary position of the discharge nozzle 28 or the direction of discharge A for the aerosol 29 can advantageously be determined.

In the embodiment shown, the nebulizer comprises an orientation projection 50 and/or an orientation recess 51. Alternatively or additionally, however, the nebulizer 26 or the insert 1 may also comprise a plurality of orientation projections 50 and/or a plurality of orientation recesses 51 and/or other means for securing the orientation, particularly the rotary orientation or rotary position, of the nebulizer 26 or the insert 1.

A rotational position of the insert 1 or nebulizer 26, in the context of the present invention, preferably, is a rotational orientation about a central axis M of the reservoir 2 or insert 1.

The reservoir 2 may be at least substantially cylindrical while the cylinder axis may correspond to the central axis M of the reservoir 2.

Particularly advantageously, the orientation projection and recess 50, 51, particularly the orientation recess 51, and the blocking device 44 may be combined with one another. In the embodiment shown in FIGS. 10 and 11, the blocking device 44 is arranged in the orientation recess 51 for this purpose. In this way, the activation of the dispensing of the medicament preparation 3 can advantageously be released only under the precondition with the blocking device 44 that the nebulizer 26 or the insert 1 has been inserted or arranged in an intended orientation.

The orientation recess 51 may be arranged on the insert 1 or on the nebulizer 26 on the end face or adjacent to the discharge nozzle 28 or the activating element 32. Alternatively or additionally, the orientation projection and recess 50, 51 may also be arranged at a different position on the nebulizer 26 or reservoir 2. For example, it is possible to arrange the orientation projection and recess 50, 51 laterally on the nebulizer 26, particularly in the form of the orientation projection 50. The orientation projection 50 may be embodied to be insertable into a groove or other guide means.

In a particularly advantageous alternative embodiment, the orientation projection 51 is in the shape of an arrow or otherwise embodied as an orientation indicator and/or as an insertion aid or is wedge-shaped. This makes it easier to insert the insert 1 into the inhaler I with the orientation projection and recess 50, 51. The inhaler I may be embodied to correspond thereto.

FIG. 12 shows a detail of the discharge nozzle 28 according to FIG. 10. The discharge nozzle 28 is preferably embodied to dispense the medicament preparation 3. Preferably the discharge nozzle 28 forms the aerosol 29 when the medicament preparation 3 is dispensed. For this purpose the medicament preparation 3 may be capable of being dispensed through discharge openings 52 in the discharge nozzle 28. The aerosol 29 may be formed by the dispensing of the medicament preparation 3 though the discharge opening 52.

As already mentioned, the medicament preparation 3 is preferably released by excess pressure in the metering chamber 10 from the valve 9 into the channel 31, when dispensing is activated. The medicament preparation 3 may be conveyed through the channel 31 to the discharge openings 52 of the discharge nozzle 28.

In the embodiment shown, the discharge openings 52 are embodied as orifices. The discharge openings 52 preferably provide a fluid connection between the outside and inside of the discharge nozzle 28. In particular, the discharge openings 52 connect the channel 31 to the environment.

Preferably, valve body 30 comprises a nozzle element 53, particularly a nozzle insert. The nozzle element 53 may cover or seal one end of the channel 31 remote from the valve 9. The nozzle insert 53 preferably comprises the discharge openings 52.

The discharge openings 52 are preferably fluidically connected to the channel 31 of the nozzle body 30. In this way, the metering chamber 10 can be fluidically connected to the discharge openings 52.

The nozzle element 53 may be pot-shaped and/or may be held in the valve body 30 by frictional and/or interlocking engagement.

In the embodiment shown, the nozzle insert 53 comprises strips 54 or an encircling strip, frame or a preferably encircling edge or a preferably encircling margin 54. The nozzle element 53 may form a pot-shape with the margin 54.

The nozzle insert 53 is preferably inserted, pushed into, clamped into or otherwise preferably sealingly attached to the nozzle body 30, particularly to the edge 54. The nozzle element 53 may be held in this way or otherwise and sealed off from the nozzle body 30 at the edges.

The discharge nozzle 28 may be embodied such that the aerosol 29 is released in a direction of dispensing A which may correspond at least substantially to the central axis of the reservoir 2. This promotes a compact construction.

Preferably, a dispensing direction A is provided which is different from the central axis M. Particularly preferably, the dispending direction A deviates from the central axis M of the reservoir 2 by more than 5°, preferably more than 10°, 15° or 20° and/or less than 50°, preferably less than 45° or 40°, particularly preferably less than 35°. This enables the dispensing direction A to be adapted to the geometry of an associated inhaler I.

The discharge openings 52 are preferably formed by orifices or bores extending diagonally to the surface or main plane of the nozzle element 53. In particular, the discharge openings may enclose a dispensing angle with the central axis M of the reservoir 2, in an opening region, which is greater than 5°, preferably greater than 10° or 15° and/or less than 50°, preferably less than 45° or 40°.

In an alternative embodiment (not shown in detail), the nozzle body 30 and/or the nozzle insert 50 may slope relative to the central axis M of the reservoir 2, preferably by more than 5° particularly more than 10° or 15° and/or less than 50°, particularly less than 45° or 40°, particularly less than 35°.

Particularly preferably, the dispensing direction A which is inclined relative to the central axis M of the reservoir 2 is produced by the discharge openings 52 and/or a sloping nozzle element 53. This enables the insert 1 to be axially inserted in an uncompleted manner in an associated inhaler I. Alternatively or additionally, the nozzle body 30 or the discharge nozzle 28 may also be inclined relative to the central axis M in order to enable to preferred direction of discharge A.

The preferred direction of discharge A may be achieved by a combination of several measures. In a preferred alternative, the discharge nozzle 28 comprises discharge openings 52 which are inclined relative to the central axis M of the reservoir 2, which can be combined with a nozzle insert 53 that is inclined relative to the central axis M. Alternatively or additionally, the nozzle body 30 may be inclined relative to the central axis M and/or the path of the discharge openings 52 may be inclined relative to the central axis M. Preferably, the preferred direction of dispensing A is achieved by the sum of the slopes provided.

An insert 1 with a combination of a direction of discharge A inclined relative to the central axis M of the reservoir 2 and the orientation projection and recess 50, 51 is particularly advantageous as in this way it is possible to prevent the aerosol 29 being dispensed in the direction of a wall, which may have the adverse effect of precipitating the medicament composition 3.

In an alternative embodiment the discharge nozzle 28 may be constructed as vortex chamber nozzle. A vortex body 56 may be provided in a vortex chamber 55 which may be formed by or at the end of the channel 31. However, other solutions are also possible for producing a vortex chamber nozzle.

The aerosol 29 which is to be formed preferably contains droplets which have such a small diameter that they are inhalable into the lungs. It has proved advantageous if the discharge nozzle 28 has a plurality of discharge openings 52. Preferably, the discharge nozzle 28 comprises at least three and preferably at least four discharge openings 52. In this way, aerosol 29 suitable for inhaling into the lungs can be produced particularly quickly. This has the advantage, particularly when the inhaler I is used on large animals, that correspondingly large quantities of dose can be converted into a respirable aerosol 29 in a relative short time. This avoids a tiresome process for achieving the total dose by numerous actuation processes.

The (respective) discharge opening 52 preferably has cross sections or minimum cross sections 57 which are less than 400 µm, preferably less than 300 µm, more particularly less than 250 µm and/or greater than 100 µm, preferably greater than 150 µm, particularly greater than 200 µm.

The discharge openings 52 may be fluidically connected to one another at the inlet end. In particular, the discharge openings 52 are joined to one another and/or to the channel 31 by supply channels 58 or other supply means 59. However, other solutions are also possible.

The discharge openings 52 preferably have accumulative outlet surface area of more than 0.1 mm$^2$, preferably more than 0.15 mm$^2$. Particularly preferably, the discharge openings 52 have accumulative outlet surface area greater than 0.2 mm$^2$, preferably greater than 0.45 mm$^2$, particularly greater than 0.6 mm$^2$ and/or less than 1.8 mm$^2$, preferably less than 1.2 mm$^2$, particularly less than 1 mm$^2$. Most particularly preferred is accumulative outlet surface area of between 0.75 mm² and 0.9 mm². As a result, particularly where there are five to six discharge openings 52, a sufficiently large quantity of the medicament preparation 3 can be dispensed or converted into the aerosol 29 in a comparatively short time, particularly in less than one second.

A cumulative outlet surface in the sense of the present invention is preferably the sum of all the outlet surfaces or (particularly hydraulic) cross sections or cross-sectional surfaces of the discharge openings 52. The respective cross section is preferably determined by the hydraulic cross section or the smallest cross section of the orifice that forms the particular discharge openings 52.

It is also preferable for the discharge nozzle 28 to be designed to dispense more than 360 μg, preferably more than 450 μg or 480 μg, particularly more than 600 μg of the medicament preparation 3 per second, particularly at an internal pressure of the reservoir 2 or a pressure on the medicament preparation 3. Alternatively or additionally, the discharge nozzle 28 is embodied to discharge less than 1500 μg per second, preferably less than 1200 μg per second or 960 μg per second, particularly less than 900 μg per second or 720 μg per second of medicament preparation 3. These values preferably relate to an internal pressure of the reservoir 2 or a pressure on the medicament preparation 3 of 3 to 6 bar, in particular 4 bar.

The medicament preparation 3 preferably has a density of more than 1.2 and/or less than 1.5 g per liter at 20° C.

The medicament preparation 3 may comprise a liquid propellant Particularly preferably, the medicament preparation 3 comprises a fluorohydrocarbon, particularly tetrafluoroethane or heptafluoropropane (HFA 134a, HFA 227 or a mixture). These have proved advantageous particularly on account of their low reactivity and their vapor pressure. The medicament preparation 3 preferably consists of more than 80% by weight, preferably more than 85 or 90% by weight, of fluorohydrocarbons, particularly of the above kind, or other propellants. As the above-mentioned propellants change into the gaseous phase as pressure decreases, a very fine, particularly pulmonary aerosol 29 can be obtained in this way.

The preferred number of more than 3, preferably more than 4 and/or less than 8, particularly less than 7 or 6 discharge openings 52 and the other properties and dimensions of the discharge nozzle 28 described may also be implemented separately in a discharge nozzle 28 or nozzle element 53 independently of the specific application described here and may be advantageously used as such.

The nozzle element 53 may be accommodated or held in a recess 61 in the nozzle body 30. The term nozzle element 53 is preferably already understood within the present invention. A nozzle insert 53 may not only be inserted in the nozzle body 30 but preferably also placed thereon or formed thereby.

FIGS. 13 to 23 show alternative embodiments for the discharge nozzle 28 which may form part of the insert 1 or inhaler I or may also be produced independently. In connection with this, it is mentioned once again that where identical reference numerals are used, identical or similar properties and advantages can be achieved, although the description has not been repeated for reasons of simplicity. Moreover, only differences from the discharge nozzle 28 according to FIG. 12 or 12*a* are described hereinafter.

In each of the following embodiments, it is particularly preferably that, as shown in FIG. 12*a* in particular, the discharge openings 52 and alternatively or additionally the nozzle body 30 and/or the nozzle element 53 may be arranged or embodied to be inclined or in some other way to produce an inclined direction of discharge A.

FIG. 13 shows a discharge nozzle 28 according to a second embodiment with an at least substantially star-shaped or snow flake-shaped nozzle element 53 which comprises the discharge openings 52 and/or forms a nozzle insert.

The nozzle element 53 may functionally correspond at least substantially to the novel element 53 according to FIGS. 12 and 12*a* and for this reason reference is particularly made to the option of an inclined direction of discharge A in describing them.

The nozzle element 53 from the embodiment shown in FIGS. 13 and 14 comprises five arm-shaped sections, each having discharge openings 52 in or on their ends. However, it is also possible to have more or fewer arm-shaped sections, for example, four or six. Optionally, a further discharge opening 52 may additionally be provided in a central region of the nozzle element 53 on which the arm-like sections are arranged.

FIG. 14 shows a perspective section through the discharge nozzle 28 from FIG. 13. The channel 31 may be connected to the discharge openings 52 by one or more supply channels 58 or other supply means 59. In the embodiment shown in FIGS. 13 and 14 the supply means 59 are preferably star-shaped.

Compared with a full-surface supply means 59, a star-shaped supply means 59 has the advantage that a reduced contact surface is available for the pressurized medicament preparation 3 and consequently force acting on the nozzle element 53 during the dispensing of the medicament preparation 3 can be kept to a minimum. This assists with the secure fixing of the nozzle element 53 to the nozzle body 30. A star-shaped supply means 59 to the respective discharge openings 52 also reduces the total volume of the supply 59 and consequently the amount of medicament preparation 3 remaining in the supply 59 which is not expelled and consequently represents a loss or may dry up.

The preferably plate-shaped nozzle element 53 in the second embodiment is preferably held in the nozzle body 30 by clamping or latching. In particular, fixing and/or sealing means are provided for holding the nozzle element 53 in the nozzle body 30 and/or for sealing the nozzle element 53 from the nozzle body 30. In particular, a circumferential bead 60 is provided which holds the nozzle element 53 against the nozzle body 30 at its edges in a clamping and/or sealing action. The bead 60 is provided on the nozzle body 30 in the embodiment shown, and in particular is integrally formed therewith. The bead 60 may, however, also be arranged on the nozzle element 53.

In the embodiment shown, the nozzle body 30 comprises a recess 61 in which the novel element 53 can be arranged. The recess 61 may comprise, on an inner, lateral and/or circumferential edge, the bead 60 for holding the nozzle element 53 by a clamping or latching action.

The bead 60 is preferably of continuous and/or circumferential configuration. In this way the nozzle element 53 can be sealed off from the nozzle body 30 and held on the nozzle body 30.

In one alternative, the bead 60 is provided on the nozzle element 53. However, other alternative possibilities are also conceivable for holding the nozzle element 53 sealingly against the nozzle body 30, for example, by adhesive bonding, clamping, latching, pressing or the like.

Holding the nozzle element 53 by means of the bead 60 is preferred as, at comparatively little expense, the nozzle element 53 is simultaneously securely fixed to the nozzle body 30 and the nozzle element 53 can be sealed off from the nozzle body 30.

FIG. 15 shows, in a third embodiment, a proposed discharge nozzle 28 with five discharge openings 52. However, it is also possible to have a different number of discharge openings 52.

FIG. 16 shows a side view of the discharge nozzle 28 according to FIG. 15. FIG. 17 shows, in a section on the line XVII-XVII from FIG. 16, the supply means 59 which in the present instance is of at least substantially star-shaped configuration.

A star-shaped supply 59 with additional fluid connections between adjacent discharge openings 52 represents a good compromise between the contact surface for the pressure and a homogenous distribution of pressure between the discharge openings 52 and a uniform discharge quantity through the respective discharge openings 52.

Adjacent discharge openings 52 may be connected to one another by connecting channels 63, preferably at the ends or on a side facing to the channel 31 or the respective discharge openings 52. In particular, ends of the supply channels 58 forming the supply 59 are connected to one another by a connecting channel 63 which is preferably at least substantially circular. In this way, a homogenous pressure distribution can be guaranteed.

In the present case, the nozzle element 53 is of a cap-shaped construction. The nozzle element 53 may be a pushed-on part or a protrusion or a cap.

The nozzle element 53 is fitted onto the nozzle body 30, preferably by clipping or latching. This has the advantage of making it easier to exchange, for example, to replace it with a nozzle element 53 having different or a different number of discharge openings 52.

FIG. 19 shows, in a third embodiment, another alternative embodiment of the proposed discharge nozzle 28 with a nozzle element 53 inserted in the nozzle body 30. The nozzle element 53 in the third embodiment is plate-shaped and preferably comprises an edge 54 for clamping, latching and/or sealing assembly.

FIG. 20 shows a side view of the discharge nozzle 28 according to FIG. 19. FIG. 21 shows a section through the discharge nozzle 28 taken along the section line XXI-XXI in FIG. 20.

As already described in connection with the second embodiment for a proposed discharge nozzle 28 from FIG. 17, an at least substantially star-shaped supply means 29 is provided which connects the channel 31 to the discharge openings 52. However, other alternative embodiments are also possible. Moreover, adjacent discharge openings 52 can additionally be fluidically connected to one another, particularly by connecting channels 63.

FIG. 22 shows a section through the discharge nozzle 28 taken along the section line XXII-XXII in FIG. 20. For reasons of simplicity, the nozzle element 53 is not shown in FIG. 22.

The nozzle body 30 may comprise a bead 60, particularly an annular bead, and/or an undercut 62, particularly a groove or annular groove, for the latching and/or clamping attachment of the nozzle element 53. These preferably correspond to one another.

The nozzle body 30 may comprise a preferably annular or disc-shaped recess 61 for accommodating the nozzle element 53. The recess 61 may comprise the undercut 62 or another bead or another connecting means suitable for a latching, clamping, interlocking and/or frictionally engaging connection.

The bead 60 and the undercut 62 may be axially offset from one another and/or provided on different sides of the recess 61. In this way, particularly secure positioning can be ensured when the nozzle element 53 is inserted.

In the embodiment shown in FIGS. 19 to 22, the nozzle element 53 is preferably in the shape of a pot. The nozzle element 53 has a plate section with the discharge openings 52 and a preferably circumferential and/or marginal collar or edge 54 which can preferably be held in the recess 61.

Figure 23:
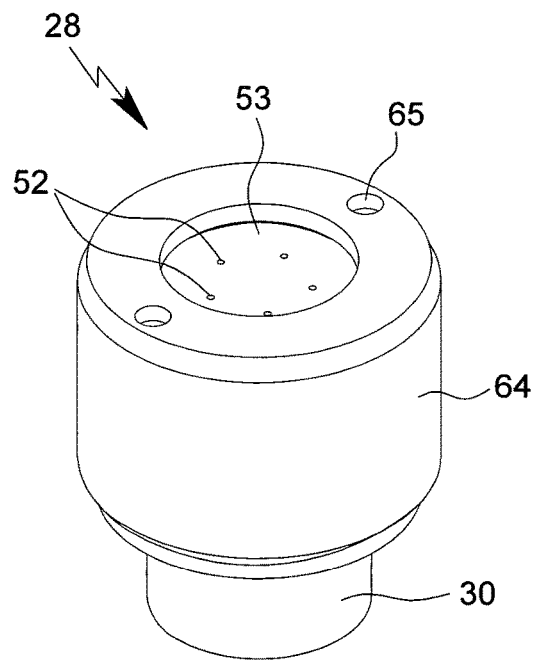
Figure 24:
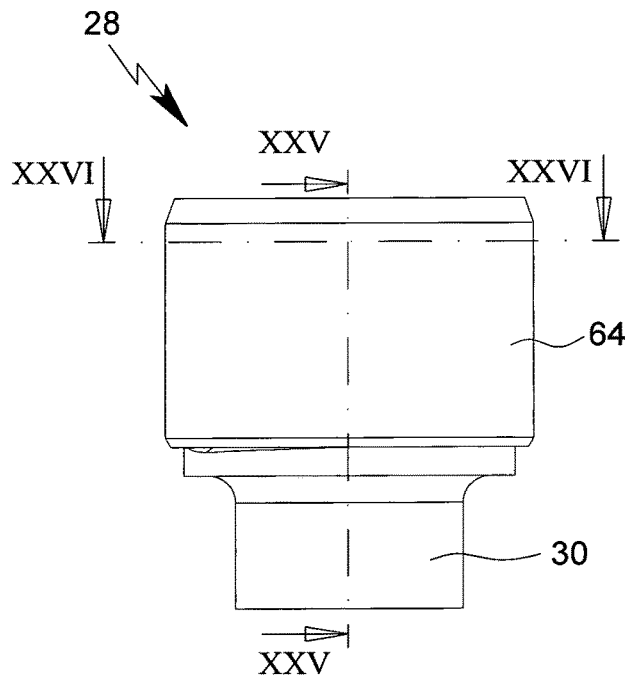
Figure 25:
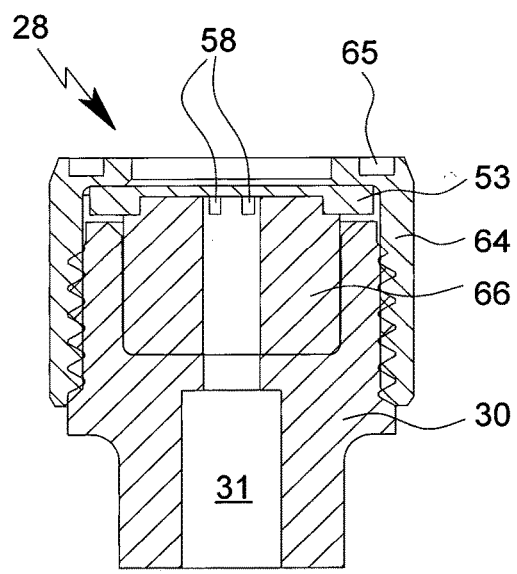
Figure 26:
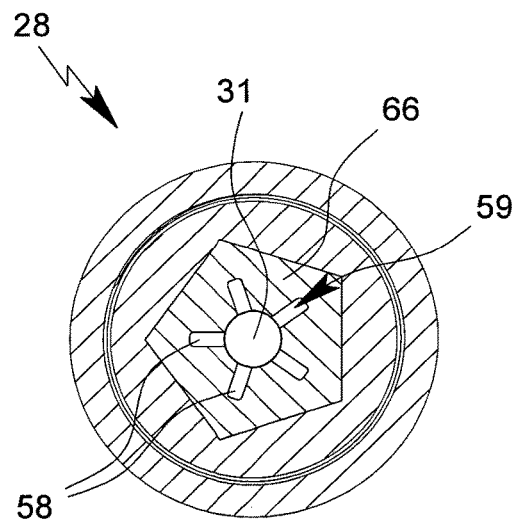

FIG. 23 shows, in perspective view, a fourth embodiment of the proposed discharge nozzle 28. FIG. 24 shows a side view of the discharge nozzle 28 according to FIG. 23. FIG. 25 shows a section through the discharge nozzle 28 of FIG. 23 taken along the section line XXIV-XXIV in FIG. 24 and FIG. 26 shows a section through the discharge nozzle 28 from FIG. 23 taken along the section line XXVI-XXVI in FIG. 24.

The discharge nozzle 28 from FIG. 23 comprises a plate-like nozzle element 53 with discharge openings 52. The nozzle element 53 is fixed to the nozzle body 30 by a lock nut 64. The lock nut 64 preferably has an internal thread which may correspond to an external thread on the nozzle body 30. The lock nut may alternatively or additionally also be latched on or otherwise secured or may be replaced by a nozzle element from the third embodiment.

The lock nut 64 may comprise mounting elements 65, particularly recesses for a tool.

The nozzle element 53 may be tightened directly against the nozzle body 30, preferably to form a seal, by the lock nut 64. In the embodiment shown, the nozzle element 53 abuts on a distributor element 66 for fluidically connecting the discharge openings 52.

The distributor element 66 may be inserted in the nozzle body 30, fitted onto the nozzle body 30 or otherwise mounted thereon or formed in one piece with the novel body. In particular, the nozzle element 53 is in contact with the nozzle body 30 by means of the distributor element 66.

In the embodiment shown, the nozzle element 53 forms a sandwich structure with the distributor element 66 and the nozzle body 30.

The lock nut 64 may preferably secure the nozzle element 53 and/or the distributor element 66 by clamping. However, other solutions are also possible.

The distributor element 66 may be elastic and/or formed from a sealing material.

The discharge nozzle 28 according to the different embodiments may also constitute separate inventive objects and may be implemented independently of the insert 1 or inhaler I.

The proposed insert 1 is preferably inserted or pushed into an inhaler I and particularly preferably received by an inhaler I. FIG. 27 shows a side view of a proposed inhaler I, particularly for a horse P.

The inhaler I may have a chamber 67 which is configured to receive and store aerosol 29. The chamber 67 may have an adaptor 68 for a respiratory orifice 69, preferably of an animal, particularly for a horse's nostril (merely indicated in FIG. 27).

The inhaler I is preferably configured to receive the reservoir 2 and particularly preferably to hold or fix it at least axially or in some other way to prevent axial movement of the reservoir 2.

Preferably, the reservoir 2 forms part of the insert 1. The insert 1 is inserted in the inhaler I in the embodiment shown in FIG. 27.

Preferably, the insert 1 or the reservoir 2 is/are fully accommodated by the inhaler I. However, it is possible for the insert 1 or the reservoir 2 to be at least partly visible or accessible from outside. Preferably, a viewing window 70, particularly an orifice, may be provided through which the insert 1 or the reservoir 2 is or are at least partly visible. In this way, a text, label or similar on the insert 1 or reservoir 2 may be visible from outside.

The inhaler I preferably comprises a counter window 71, particularly an orifice, or other means for indicating the status of a counter or the display device 36 of the counter 34. In particular, the counter 34 is provided in the insert 1 and can be seen through the counter window 71.

Figure 28:
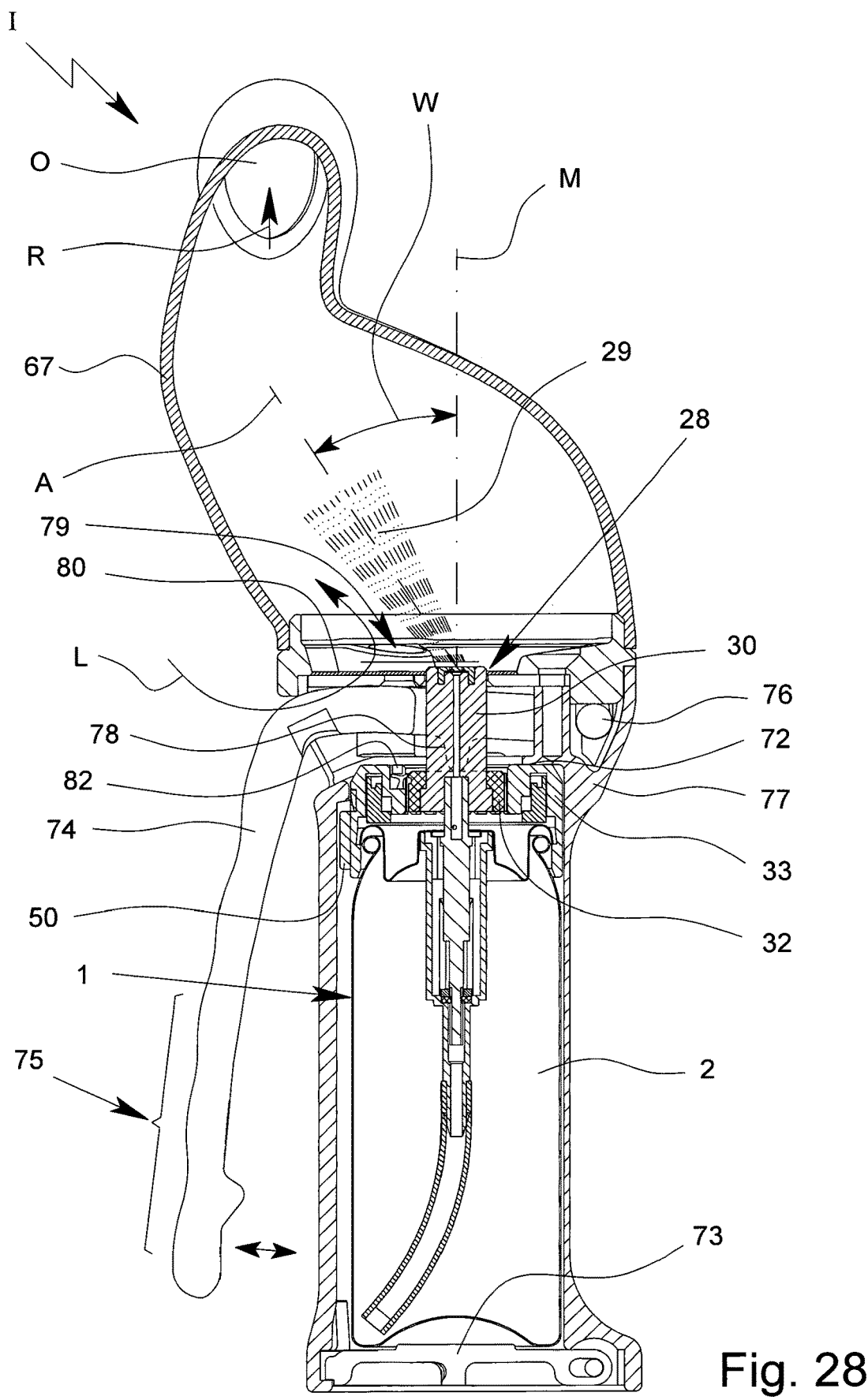

FIG. 28 shows a section through the proposed inhaler I taken along the section line XXVIII-XXVIII in FIG. 27 with the insert 1 in the position of use.

In the embodiment according to FIG. 28, the insert 1 has been inserted in the inhaler I. In particular, the reservoir 2 is arranged in the inhaler I or at least substantially accommodated by the inhaler I.

The reservoir 2 can be at least axially fixed, held or otherwise secured against axial movement in or on the inhaler I.

Preferably, the reservoir 2 is axially secured via or by means of the nebulizer 26.

Preferably, the insert 1 is held between retaining surfaces. In the embodiment shown, the inhaler I has a stop 72 against which the nebulizer 26, the insert 1 and/or the reservoir 2 may lie.

Preferably the housing 33 of the nebulizer 26 abuts directly on the stop 72. In this way axial movement of the reservoir 2 can be prevented at least in one direction.

Preferably, the reservoir 2 or the insert 1 is also secured against axial movement on the side remote from the stop 72. In the embodiment shown in FIG. 28, the inhaler I comprises a flap or other retaining portion 73 in order to form an abutment for the reservoir 2 of the insert 1.

The combination of the stop 72 and the retaining portion 73 is able to axially secure the insert 1 or reservoir 2. However, alternative solutions are also possible, such as for example, a clamping or latching fixing or holding of the insert 1.

The insert 1 can preferably be inserted in the inhaler I, removed from the inhaler I and/or replaced. For this purpose the retaining portion 73 may be of flap-like construction or capable of being opened and/or closed by some other means.

The insert 1 may be insertable into the inhaler I together with the discharge nozzle 28.

The retaining portion 73 may be opened for the insertion of the insert 1 and then closed and/or locked again. By locking the retaining portion 73 the position of the reservoir 2 can be fixed or the reservoir 2 can be fixed.

In an alternative (not shown) the retaining portion 73 is produced by other interlocking means or a fixing element. For example, the retaining portion 73 comprises an engaging lug (not shown) or is formed as an engaging lug which can hold the reservoir 2 or insert 1 by latching and/or prevent axial movement of the reservoir 2 in the direction away from the stop 72.

The reservoir 2 or insert 1 may also be held solely by a stop 72 and/or without abutments, for example, by clamping.

The reservoir 2 preferably comprises a valve 9 arranged on the top in the position of use of the inhaler I. The reservoir 2 is thus preferably used upright or is intended for (exclusively) upright use.

In the embodiment shown, the reservoir 2 comprises an immersion tube 21 through which the medicament preparation 3, which is arranged in the reservoir 2 and can be immersed in the medicament preparation 3. By means of the immersion tube 21 the medicament preparation 3 can be forced into the valve 9, preferably by means of the propellant 4, particularly propellant gas.

The inhaler I may comprise a preferably lever-like actuating element 74. The actuating element 74 is preferably designed to activate dispensing of the aerosol 29. The actuating element 74 may at the same time cause an, in particular, axial movement of the valve element 11 of the valve 9, by means of which the medicament preparation 3 can be dispensed through the discharge nozzle 28.

In the embodiment shown the actuating element 74 is embodied as an actuating lever.

The actuating element 74 may be hinged to one side of the valve 9 or the discharge nozzle 28 and on the other or opposite side of the valve 9 or discharge nozzle 28 it may have an actuating section 75.

In the embodiment shown, the actuating element 74 comprises a joint 76 by which the actuating element 74 is preferably jointed to the inhaler I or on or in an inhaler housing 77 of the inhaler I.

The actuating element 74 is preferably configured so as to embrace the discharge nozzle 28 or the valve element 11. The actuating element 74 has, in particular, a recess in which the discharge nozzle 28 can be arranged, is arranged in a fork shape around the discharge nozzle 28 or the valve element 11 or is otherwise configured to engage around the discharge nozzle 28 of the valve element 11. This advantageously makes it possible to actuate the valve 9 symmetrically, as will be described in more detail hereinafter.

The actuating element 74 may comprise one or more actuating parts 78 which are configured to move the actuating element 74, the discharge nozzle 28 or the nozzle body 30 of the nebulizer 26 in the axial direction, in particular.

In the embodiment shown, the actuating element 74 comprises two actuating parts 78. The actuating parts 78 are preferably configured to exert a force on the activating element 32, the discharge nozzle 28 or the nozzle body 30 in order to move the valve element 11 preferably in the axial direction. In this way, the valve 9 can be opened and the medicament preparation 3 dispensed.

The actuating element 74 preferably comprises two actuating portions 78, particularly arranged on opposite sides of the discharge nozzle 28. The actuating portion or portions 78 may comprise projections or be configured as projections. In the embodiment shown, one of the actuating portions 78 is located behind the section plane and is therefore merely indicated by dashed lines. A second one of the actuating portions 78 is located in front of the section plane and is therefore not shown.

The actuating portions 78 are preferably arranged symmetrically to the discharge nozzle 28, to the valve stem 12 and/or to the channel 31. In this way it can be ensured that the discharge nozzle 28 does not slope, or slopes only to an insignificant extent, during the actuation process. Advantageously, jamming, wear and other types of malfunction can thus be prevented.

The actuating portion 78 or the actuating portions 78 may have a rounded tip or a rounded end which preferably faces or is adjacent to the activating element 32, the discharge nozzle 28 or the nozzle body 30. This allows the actuating portion(s) 78 to slide along in a low-friction manner. In this way, reliable operation and a long service life of the inhaler I can be achieved.

For operation, the actuating element 74 may be moved on or with the actuating section 75, particularly in the direction of the inhaler I or the inhaler housing 77. This movement can be guided by means of the joint 76 and preferably leads to a movement of the actuating portion 78 or actuating portions 78 which at least includes an axial component. As a result of the movement of the actuating portion 78 or actuating portions 78, the activating element 32, the discharge nozzle 28 or the nozzle body 30 may preferably be moved axially, thus enabling the valve 9 to be opened. Theoretically, however, other solutions are also possible for the actuation.

In an alternative embodiment which is not shown here, the actuating element may comprise a wedge or a slide or be otherwise configured so that on activation it can preferably move the activating element 32, the discharge nozzle 28 or the nozzle body 30 axially, so as to enable the valve 9 to be opened.

In other alternatives, electrical or electromechanical opening methods are possible. For example, a solenoid may be provided which is able to activate the dispensing of medicament preparation 3. In such solutions, there is no need for the provision of an (axially) movable valve element 9, an (axially) movable activating element 32, an (axially) movable discharge nozzle 28 and/or an (axially) movable nozzle body 30.

The chamber 2 for holding and temporarily storing aerosol 29 preferably comprises an inlet opening 79 through which air L can enter.

The discharge openings 52 are preferably arranged in the chamber 67. The aerosol 29 may in this way be formed directly in the chamber 67. Alternatively, the discharge openings 52 may be arranged in front of the inlet opening 79. In this case, it is preferable if the aerosol 29 can enter the respiratory orifice 69 through the inlet opening 79.

The inlet opening 79 may comprise an inhalation valve 80. The inhalation valve 80 is preferably embodied as a non-return valve. The inhalation valve 80 may be biased into the closed position or be self-closing in some other way.

The inhalation valve 80 can be opened to the atmosphere by negative pressure in the chamber 67, as a result of which air L is able to flow into or towards the chamber 67.

During an exhalation process in the direction of the chamber 67, an excess pressure may be produced in the chamber 67. When there is excess pressure in the chamber 67, the inhalation valve 80 preferably closes automatically. This at least prevents excess contamination of the chamber 67 with secretions or the like. Also, it ensures that aerosol 29 temporarily stored in the chamber 67 is not blown out through the inlet opening 79. This ensures reliable and accurate dosing.

The chamber 67 preferably comprises a dispensing opening O in the region of the adapter 68 for the respiratory orifice 69. Aerosol 29 can be dispensed through the dispensing opening O. At the same time, to equalize the pressure, air 85 can flow through the inlet opening 79 into the respiratory orifice 69.

It is preferable if the dispensing opening O is laterally offset relative to the discharge nozzle 28 or the inlet opening 79 and/or is provided laterally of the chamber 67. This advantageously provides a continuous transition to the respiratory orifice 69, particularly in horses P or other large animals.

It is preferable if the central axis 11 of the reservoir 2 or the insert 1 or the direction of inflow of air L is skewed in relation to a direction of dispensing R through the dispensing opening O.

In the embodiment according to FIG. 28 the direction of discharge A of the discharge nozzle 28 or for the aerosol 29 is inclined relative to a central axis M of the reservoir 2 or of the insert. In particular, the direction of discharge A and/or a straight line running through the dispensing opening R and the nozzle element 53 or the discharge nozzle 28 encloses with the central axis M and/or a dispensing angle W which is greater than 5°, preferably greater than 10°, particularly greater than 15° and/or less than 50°, preferably less than 45° or 40°, particularly less than 35°. This results in an increased free length of travel for the aerosol 29, thus decreasing the probability of aerosol ingredients or medicament preparation 3 being deposited on the walls of the chamber 67. This leads to improved and more accurate dosage.

Figure 29:
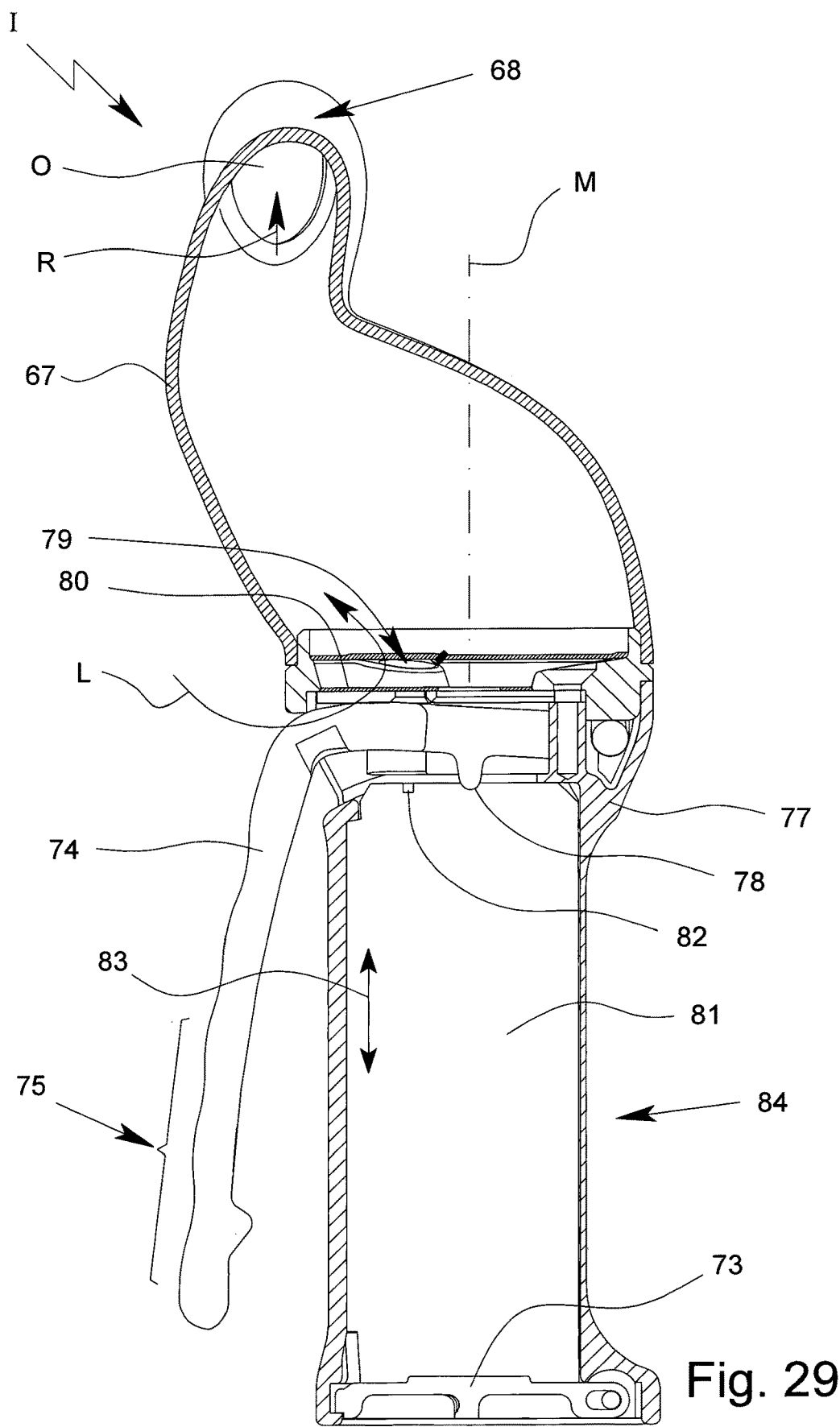

FIG. 29 shows the proposed inhaler I without the insert 1.

The inhaler 1 preferably comprises a holder 81 into which the reservoir 2 or the insert 1 can be inserted. Particularly preferably, the insert 1 or the reservoir 2 can be inserted, particularly pushed, into the holder 81 axially and/or with the nebulizer 26 or the discharge nozzle 28 at the front.

It is preferable if the insert 1 can only be inserted in the holder 81 in a specific direction, enabling the aerosol to be dispensed in or through the chamber 67.

It is preferable if the insert 1 or the nebulizer 26 can only be inserted into the holder 81 in a specific rotary position. This ensures that the direction of discharge A corresponds to the shape of the chamber 67. Alternatively or additionally, determining a rotary position of the insert 1 or the nebulizer 26 makes it possible to obtain a defined alignment of the window 35 for the counter 34. This ensures that the counter window 71 and the window 35 of the counter 34 are congruent or otherwise correspond to one another, so that the counter 34 is visible or readable.

The holder 81 preferably comprises an orientation and/or release portion 82.

The orientation and/or release portion 82 may be configured so as to fix the orientation, particularly rotary orientation, of the insert 1 in the inhaler I and/or to enable activation of the dispensing of the medicament preparation 3.

The orientation and/or release portion 82 is particularly configured to correspond to the orientation projection and recess 50, 51 of the insert 1, particularly to the orientation recess 51. Particularly preferably, the orientation and/or release portion 82 is arranged and configured to be complementary to the orientation device 50, 51, particularly to the orientation recess 51.

The insert 1 can preferably only be fully inserted into the holder 81 of the inhaler I, or the position of use of the insert 1 can only be achieved, when the orientation and/or release portion 82 is in alignment with the orientation recess 51 or when the orientation and/or release portion 82 is arranged directly opposite the orientation recess 51. In this case, the orientation and/or release portion 82 can be inserted into the orientation recess 51, thus enabling the insert 1 to reach a position of use in the holder 81.

The orientation and/or release portion 82 may alternatively or additionally be used to release the dispensing of the medicament preparation 3. The orientation and/or release portion 82 may for this purpose act on the blocking device 44 of the insert 1 and thereby remove a blocking arrangement preventing, in particular, axial movement of the activating element 32, the nozzle body 30, the discharge nozzle 28 and/or the valve element 11. In this way the orientation and/or release portion 82 can allow the formation of aerosol.

When the insert 1 is inserted into the holder 81, the orientation and/or release portion 82 may both determine an orientation of the insert 1 in the holder 81 and also cause release of the aerosol production. For this purpose, the orientation and/or release portion may be capable of being inserted or pushed into the orientation recess 51 only in the intended orientation or rotary orientation, thus releasing the blocking device 44. However, it is also possible for the orientation and/or release portion 82 simply to determine the orientation or release the dispensing of the medicament preparation 3.

The inhaler I, particularly the holder 81, may comprise an orientation section 83. Preferably, the orientation section 83 has a guide, a groove, a notch or other structure which corresponds to the orientation projection 50 or other orientation device 50, 51 of the insert 1. In this way, the rotary position of the insert in the inhaler I or in the holder 81 can be fixed.

In the embodiment shown in FIG. 28, the insert 1 is inserted in oriented manner into the holder 81, with the orientation projection 50 engaging in the orientation section 83 and/or the orientation and/or release portion 82 engaging in the orientation recess 51 and thus particularly preferably acting on the blocking device 44 so that the aerosol formation can be initiated.

The orientation and/or release portion 82 and the orientation projection 50 or the orientation section 83 and the orientation arrangement 51 preferably correspond to one another, preferably so that the insert 1 or the nebulizer 26 can only be inserted into the holder 81 or reach its position of use in a particular rotary position. Theoretically, however, two or more specific rotary positions may be made possible or permitted.

The orientation and/or release portion 82 may be formed within the holder 81 and/or by a projection on the stop 72. This ensures that an insert 1 that is twisted or otherwise wrongly oriented or a twisted or wrongly oriented nebulizer 26 cannot be inserted fully into the holder 81 or up to the stop 72. This ensures that the (rotary) orientation of the insert 1 or the nebulizer 26 in the holder 81 corresponds to an intended (rotary) orientation.

Preferably, the retaining portion 73 is configured such that it only holds or retains the reservoir 2 or the insert 1, and in particular the flap can only be closed and/or locked, when the insert 1 or the nebulizer 26 is inserted into the holder 81 completely or in oriented manner. This prevents the dispensing of the medicament preparation 3 from being initiated when the nebulizer 26 is inserted incompletely and/or in the incorrect orientation or when the insert 1 is inserted incompletely and/or in the incorrect orientation.

During the insertion of the insert 1 or the nebulizer 26 the orientation and/or release portion 82 may exert a force F on the blocking device 44, particularly only when the insert 1 is inserted in an intended rotary position. As a result, the blocking device 44 may be bent, deformed or otherwise acted upon to permit the dispensing of the medicament preparation 3 to be initiated.

In particular, the orientation and/or release portion 82, particularly as described in conjunction with FIG. 11, may release an axial movement of the activating element 32, the nozzle body 30 and/or the discharge nozzle 28. The release can enable an axial movement, in particular, of the valve element 11 or actuation of the valve 9. The actuating element 74 may be used for this purpose.

Other forms of blocking devices 44 and corresponding release portions are also possible. For example, a locking bolt or rod may be provided as a blocking device 44 and the orientation and/or release portion 82 or some other release portion may remove a blocking arrangement caused by the locking bolt or rod and release the dispensing of the medicament preparation 3.

In the embodiment in FIG. 29, the holder 81 is formed in a handle 84 of the inhaler I. In this way, it is possible to obtain a compact inhaler I with a robust handle 84, while the handle 84 protects the insert 1 and enables it to be operated even when wearing gloves.

For activating the dispensing of the medicament preparation 3 or for actuating the valve 9, the actuating element 74 may be hinged to the handle 84. This enables the opening of the valve 9 and dispensing of the medicament preparation as an aerosol to be carried out particularly with the actuating portion(s) 78. However, other alternative embodiments are also possible.

The proposed inhaler I may also be produced separately or without the insert 1 and constitute an independent aspect of the invention.

What is claimed is:

1. An insert that is insertable into an inhaler, comprising:
   a reservoir containing a medicament preparation held under pressure,
   a valve, and
   a nebulizer held directly on the reservoir, and having a discharge nozzle associated therewith and fluidically connected to the valve, for forming an aerosol with the medicament preparation, and
   further comprising an orientation device which allows initiation of the dispensing of the medicament preparation only in a specified rotational position or orientation of the nebulizer about a central axis of the reservoir, making it possible to fix an angular direction of discharge of the discharge nozzle into the inhaler in use.

2. The insert according to claim 1, wherein the nebulizer is inseparably held on the reservoir.

3. The insert according to claim 1, wherein the discharge nozzle is held in at least one of axially movable and inseparable manner on the reservoir by means of the nebulizer.

4. The insert according to claim 1, further comprising a counter which is driven by initiating dispensing of a medicament preparation.

5. The insert according to claim 1, further comprising a blocking device which is configured to at least one of prevent accidental initiation, initiation prior to insertion of the insert into an inhaler, and initiation after a predetermined number of initiation processes has been reached or exceeded.

6. The insert according to claim 1, wherein the insert is configured to dispense the aerosol of the medicament preparation from the discharge nozzle in a direction of discharge which extends diagonally with respect to the central axis of the reservoir.

7. The insert according to claim 6, wherein the direction of discharge is inclined by more than 5° relative to the central axis of the reservoir.

8. The insert according to claim 1, wherein the discharge nozzle comprises at least 3 discharge openings.

9. The insert according to claim 1, wherein the discharge nozzle comprises discharge openings with a cumulative outlet surface area of more than 0.2 mm$^2$.

10. The insert according to claim 1, further comprising an axially movable activating element with which the medicament preparation is able to be dispensed by movement of the activating element.

11. The insert according to claim 10, further comprising a counter which is driven by initiating dispensing of a medicament preparation, wherein the counter is driveable by the movement of the activating element.

12. The insert according to claim 10, wherein the activating element is adapted to be released by total insertion of the insert in the intended orientation.

13. The insert according to claim 10, wherein the insert or the nebulizer comprises a frame or a shoulder which is immovable relative to the reservoir, wherein the activating element is adjacent to the frame or shoulder.

14. The insert according to claim 13, wherein the frame or shoulder surrounds, encloses or embraces the activating element.

15. The insert according to claim 13, wherein the discharge nozzle is axially movable in the nebulizer.

16. The insert according to claim 1, wherein the discharge nozzle is part of the nebulizer.

17. Inhaler, comprising:
an inhaler body, and an insert with a reservoir containing a medicament preparation held under pressure and insertable into the inhaler body, a valve, and a nebulizer held directly on the reservoir, and having a discharge nozzle associated therewith and fluidically connected to the valve, for forming an aerosol with the medicament preparation, wherein the inhaler comprises an orientation portion for fixing the rotational orientation of the insert about a central axis of the reservoir.

18. Inhaler according to claim 17, wherein the inhaler comprises a chamber for holding and temporarily storing aerosol.

19. Inhaler according to claim 17, wherein the inhaler comprises a lever-shaped actuating element.

20. Inhaler, comprising a holder for receiving an insert having a reservoir containing a medicament preparation held under pressure, a valve, and a nebulizer held directly on the reservoir, and having a discharge nozzle associated therewith and fluidically connected to the valve, for forming an aerosol with the medicament preparation, wherein the inhaler comprises an orientation portion for fixing the rotational orientation of the insert about a central axis of the reservoir.

21. Inhaler according to claim 20, wherein the inhaler comprises a chamber for holding and temporarily storing aerosol.

22. Inhaler according to claim 20, wherein the inhaler comprises a lever-shaped actuating element.

23. An insert that is insertable into an inhaler, comprising:
a reservoir containing a medicament preparation held under pressure,
a valve, and
a nebulizer held directly on the reservoir, and having a discharge nozzle associated therewith and fluidically connected to the valve, for forming an aerosol with the medicament preparation, and
the insert further comprising a blocking device which is configured to at least one of prevent accidental initiation, initiation prior to insertion of the insert into an inhaler.

24. An insert that is insertable into an inhaler, comprising:
a reservoir containing a medicament preparation held under pressure,
a valve, and
a nebulizer held directly on the reservoir, and having a discharge nozzle associated therewith and fluidically connected to the valve, for forming an aerosol with the medicament preparation,
wherein the insert is configured to dispense the medicament preparation in a direction of discharge of the aerosol from the discharge nozzle which extends diagonally with respect to the central axis of the reservoir, and
wherein said direction of discharge causes a central axis of the aerosol formed to be inclined by more than 5° and less then 50° relative to the central axis of the reservoir.

25. The insert according to claim 24, wherein said angle of discharge is less than 35°.

26. The insert according to claim 24, wherein said angle of discharge is more than 15°.

* * * * *